US007485774B2

(12) United States Patent
Metzlaff et al.

(10) Patent No.: US 7,485,774 B2
(45) Date of Patent: Feb. 3, 2009

(54) METHODS AND MEANS FOR DELIVERING INHIBITORY RNA TO PLANTS AND APPLICATIONS THEREOF

(75) Inventors: Michael H. Metzlaff, Tervuren (BE); Veronique M. L. Gosselé, Ghent (BE); Frank Meulewaeter, Melle (BE); Ina C. A. Faché, Oosterzele (BE)

(73) Assignee: Bayer BioScience, N.V., Gent (BE)

( * ) Notice: Subject to any disclaimer, the term of this patent is extended or adjusted under 35 U.S.C. 154(b) by 414 days.

(21) Appl. No.: 10/321,434

(22) Filed: Dec. 18, 2002

(65) Prior Publication Data

US 2003/0135882 A1 Jul. 17, 2003

Related U.S. Application Data

(60) Provisional application No. 60/340,488, filed on Dec. 18, 2001.

(51) Int. Cl.
*C12N 15/82* (2006.01)
*C12N 15/83* (2006.01)
*C12N 15/84* (2006.01)
*C12N 15/87* (2006.01)

(52) U.S. Cl. .................... 800/285; 435/320.1; 800/286; 800/294

(58) Field of Classification Search ....................... None
See application file for complete search history.

(56) References Cited

U.S. PATENT DOCUMENTS 5,034,323 A 7/1991 Jorgensen et al.
5,190,931 A 3/1993 Inouye
5,204,731 A 4/1993 Tanaka et al.
5,304,731 A 4/1994 Masuta et al.
5,500,360 A 3/1996 Ahlquist et al.
5,849,891 A 12/1998 Lin et al.
5,922,602 A * 7/1999 Kumagai et al. ............ 435/468

FOREIGN PATENT DOCUMENTS

EP 1087017 A2 3/2001
WO WO90/12107 10/1990
WO WO93/03161 2/1993
WO WO95/34668 12/1995
WO WO98/36083 8/1998
WO WO98/53083 11/1998
WO WO99/36516 7/1999
WO WO00/63397 10/2000

OTHER PUBLICATIONS

Grimsley et al., PNAS, 1986, vol. 83, pp. 3282-3286.*
Kurath et al., J. Gen. Virol., 1993, vol. 74, pp. 1233-1243.*
Thomas et al., Plant J., 2001, vol. 25, pp. 417-425.*
Baulcombe et al, "Virus-induced Gene Silencing" *JIC & SL Annual Report* (1996/97), p. 50.
Malcuit et al, *Poster S22-67, 6th International Congress of Plant Molecular Biology,* Quebec, Jun. 18-24, 2000, Abstract, p. 522.
Chapman, Ph.D. Dissertation, "A Molecular Analysis of Potato Virus X", University of Cambridge, UK (1991), p. 1-195.
Iraida Amaya et al, "Expression of Centroadialis (CENO and CEN-like Genes in Tobacco Reveals a Conserved Mechanism Controlling Phase Change in Diverse Species" *The Plant Cell* vol. 11, 1405-1417, Aug. 1999, The American Society of Plant Physiologists.
David C. Baulcombe, "Mechanisms of Pathogen-Derived Resistance to Viruses in Transgenic Plants", *The Plant Cell,* vol. 8, 1833-1844, Oct. 1996, American Society of Plant Physiologists.
David C. Baulcombe, "Fast Forward Genetics Based on Virus-Induced Gene Silencing", *Current Opinion in Plant Biology* 1999, vol. 2, 109-113, Elsevier Science Ltd ISSN 1369-5266.
Rachel A. Burton et al., "Virus-Induced Silencing of a Plant Cellulose Synthase Gene", *The Plant Cell,* vol. 12, 691-705, May 2000, American Society of Plant Physiologists.
Ann Depicker et al., "Post-Transcriptional Gene Silencing in Plants", *Current Opinion in Cell Biology,* 1997, vol. 9, 373-382, Current Biology Ltd ISSN 0955-0674.
James J. English, Suppression of Virus Accumulation in Transgenic Plants Exhibiting Silencing of Nuclear Genes, *The Plant Cell,* vol. 8, 179-188, Feb. 1996, American Society of Plant Physiologists.
James J. English, "Requirement of Sense Transcription of for Homology-Dependent Virus Resistance and Trans-Inactivation", *The Plant Journal,* 1997, vol. 12, No. 3, 597-603.
Andrew J. Hamilton et al., "A Transgene With Repeated DNA Causes High Frequency, Post-Transcriptional Suppression of ACC-Oxidase Gene Expression in Tomato", *The Plant Journal* 1998, vol. 15, No. 6, 737-746.
Stefan Henkes et al., "A Small Decrease of Plastid Transketolase Activity in Antisense Tobacco Transformants Has Dramatic Effects on Photosynthesis and Phenylpropanoid Metabolism", *The Plant Cell,* vol. 13, 535-551, Mar. 2001, American Society of Plant Physiologists.
M.H. Kumagai et al., "Cytoplasmic Inhibition of Carotenoid Biosynthesis With Virus-Derived RNA", *Proc. natl. Acad. Sci. USA,* vol. 92, 1679-1683, Feb. 1995, Genetics.
M. Teresa Ruiz et al., "Initiation and Maintenance of V irus-Induced Gene Silencing", *The Plant Cell,* vol. 10, 937-946, Jun. 1998, American Society of Plant Physiologists.
Maike Stam et al, "The Silence of Genes in Transgenic Plants", *Annals of Botany,* vol. 79, 3-12, 1997, Annals of Botany Company.
Peter M. Waterhouse et al, "Virus Resistance and Gene Silencing in Plants Can be Induced by Simultaneous Expression of Sense and Antisense RNA", *Proc. Natl. Acad. Sci. USA,* vol. 95, 13959-13964, Nov. 1998, The National Academy of Sciences 0027-8424/98/9513959.
Gossele V., Fache I., Cornelissen M. and Matzlaff, M., "SVISS—A Novel Transient Gene Silencing System for Gene Function Discovery and Validation in Tobacco Plants", *The Plant Journal,* vol. 32 (issue 5), pp. 859-866 (2002), Blackwell Sciences Ltd., Oxford, UK.
F. Ratcliff et al., "Tobacco Rattle Virus as a Vector for Analysis of Gene Function by Silencing", The Plant Journal (2001) vol. 25, No. 2, pp. 237-245, Blackwell Science Ltd., Oxford, England.

* cited by examiner

*Primary Examiner*—Ashwin Mehta
(74) *Attorney, Agent, or Firm*—Buchanan Ingersoll & Rooney PC

(57) ABSTRACT

The invention provides improved methods and means for introducing inhibitory RNA into plant cells. The invention also provides kits comprising viral RNA vectors derived from satellite viruses and corresponding helper viruses for the introduction of inhibitory RNA into plant cells and plants. Further, the invention comprises methods for obtaining an enhanced or improved gene-silencing phenotype.

24 Claims, No Drawings

SEQUENCE LISTING

```
<160> NUMBER OF SEQ ID NOS: 18

<210> SEQ ID NO 1
<211> LENGTH: 1059
<212> TYPE: DNA
<213> ORGANISM: Artificial
<220> FEATURE:
<223> OTHER INFORMATION: cDNA sequence of the genome of satellite
      tobacco mosaic virus cloned into pSTMV-1

<400> SEQUENCE: 1

agtaaaactt accaatcaaa gacctaacca acaggactgt cgtggtcatt tatgctgttg      60

ggggacatag ggggaaaaca tattgccttc ttctacaaga ggccttcagt cgccataatt     120

acttggcgcc caattttggg tttcagttgc tgtttccagc tatggggaga ggtaaggtta     180

aaccaaaccg taaatcgacg ggtgacaatt cgaatgttgt tactatgatt agagctggaa     240

gctatcctaa ggtcaatccg actccaacgt gggtcagagc catacctttc gaagtgtcag     300

ttcaatctgg tattgctttt aaagtaccgg tcgggtcact attttcggca aatttccgga     360

cagattcctt tacaagcgtc acagtgatga gtgtccgtgc ttggacccag ttaacaccgc     420

cagtaaatga gtacagtttt gtgaggctga agccattgtt caagactggt gactctactg     480

aggagttcga agagcgtgca tcaaacatca acacacgagc ttctgtaggg tacaggattc     540
```

```
caactaattt gcgtcagaat actgtggcag ccgacaatgt atgcgaagta agaagtaact    600

gtcgacaagt cgccttggtt atttcgtgtt gttttaactg aacctcgaca taagcctttt    660

ggatcgaagg ttaaacgatc cgctcctcgc ttgagcttga ggcggcgtat ctcttatgtc    720

aacagagaca ctttggtcta tggttgtata acaatagata gactcccgtt tgcaagatta    780

gggttaacag atcttgccgt tagtctggtt agcgcgtaac cggccttgat ttatggaata    840

gatccattgt ccaatgggct ttgccaatgg aacgccgacg tggctgtata atacgtcgtt    900

gacaagtacg aaatcttgtt agtgtttttc cctccactta aatcgaaggg ttttgttttg    960

gtcttcccga acgcatacgt tagtgtgact accgttgttc gaaacaagta aaacaggaag   1020

ggggttcgaa tccctcccta accgcgggta agcggccca                          1059
```

```
<210> SEQ ID NO 2
<211> LENGTH: 1058
<212> TYPE: DNA
<213> ORGANISM: Artificial
<220> FEATURE:
<223> OTHER INFORMATION: cDNA sequence of the genome of satellite
      tobacco mosaic virus

<400> SEQUENCE: 2

agtaaactta ccaatcaaaa gacctaacca acaggactgt cgtggtcatt tatgctgttg     60

ggggacatag ggggaaaaca tattgccttc ttctacaaga ggccttcagt cgccataatt    120

acttggcgcc caattttggg tttcagttgc tgtttccagc tatgggggaga ggtaaggtta    180

aaccaaaccg taaatcgacg ggtgacaatt cgaatgttgt tactatgatt agagctggaa    240

gctatcctaa ggtcaatccg actccaacgt gggtcagagc catacctttc gaagtgtcag    300

ttcaatctgg tattgctttt aaagtaccgg tcgggtcact attttcggca aatttccgga    360

cagattcctt tacaagcgtc acagtgatga gtgtccgtgc ttggacccag ttaacaccgc    420

cagtaaatga gtacagtttt gtgaggctga agccattgtt caagactggt gactctactg    480

aggagttcga agggcgtgca tcaaacatca acacacgagc ttctgtaggg tacaggattc    540

caactaattt gcgtcagaat actgtggcag ccgacaatgt atgcgaagta agaagcaact    600

gtcgacaagt cgccttggtt atttcgtgtt gttttaactg aacctcgaca taagcctttt    660

ggatcgaagg ttaaacgatc cgctcctcgc ttgagcttga ggcggcgtat ctcttatgtc    720

aacagagaca ctttggtcta tggttgtata acaatagata gactcccgtt tgcaagatta    780

gggttaacag atcttgccgt tagtctggtt agcgcgtaac cggccttgat ttatggaata    840

gatccattgt ccaatggctt tgccaatgga acgccgacgt ggctgtataa tacgtcgttg    900

acaagtacga aatcttgtta gtgtttttcc ctccacttaa atcgaagggt tttgttttgg    960

tcttcccgaa cgcatacgtt agtgtgacta ccgttgttcg aaacaagtaa aacaggaagg   1020

gggttcgaat ccctccctaa ccgcgggtaa gcggccca                           1058
```

```
<210> SEQ ID NO 3
<211> LENGTH: 2346
<212> TYPE: DNA
<213> ORGANISM: Artificial
<220> FEATURE:
<223> OTHER INFORMATION: cDNA sequence of  L. esculentum (tomato)
      phytoene desaturase

<400> SEQUENCE: 3

cttttactag ttatagcatt cggtatcttt ttctgggtaa ctgccaaacc accacaaatt     60
```

-continued

```
acaagtttcc atttaactct tcaacttcaa cccaaccaaa tttatttcct taattgtgca    120
gaaccactcc ctatatcttc taggtgcttt cattcgttcc gaggtaagaa aagatttttg    180
tttctttgaa tgctttatgc cactcgttta acttctgagg tttgtggatc ttttaggcga    240
ctttttttt ttttgtatgt aaaatttgtt tcataaatgc ttctcaacat aaatcttgac    300
aaagagaagg aattttacca agtatttagg ttcagaaatg gataattttc ttactgtgaa    360
atatccttat ggcaggtttt actgttattt ttcagtaaaa tgcctcaaat tggacttgtt    420
tctgctgtta acttgagagt ccaaggtagt tcagcttatc tttggagctc gaggtcgtct    480
tctttgggaa ctgaaagtcg agatggttgc ttgcaaagga attcgttatg ttttgctggt    540
agcgaatcaa tgggtcataa gttaaagatt cgtactcccc atgccacgac cagaagattg    600
gttaaggact tggggccttt aaaggtcgta tgcattgatt atccaagacc agagctggac    660
aatacagtta actatttgga ggctgcattt ttatcatcaa cgttccgtgc ttctccgcgc    720
ccaactaaac cattggagat tgttattgct ggtgcaggtt tgggtggttt gtctacagca    780
aaatatttgg cagatgctgg tcacaaaccg atactgctgg aggcaaggga tgttctaggt    840
ggaaaggtag ctgcatggaa agatgatgat ggagattggt acgagactgg tttgcatata    900
ttctttgggg cttacccaaa tattcagaac ctgtttggag aattagggat taacgatcga    960
ttgcaatgga aggaacattc aatgatattt gcaatgccaa gcaagccagg agaattcagc   1020
cgctttgatt tctccgaagc tttacccgct cctttaaatg gaattttagc catcttaaag   1080
aataacgaaa tgcttacatg gccagagaaa gtcaaatttg caattggact cttgccagca   1140
atgcttggag ggcaatctta tgttgaagct caagatggga taagtgttaa ggactggatg   1200
agaaagcaag gtgtgccgga cagggtgaca gatgaggtgt tcattgctat gtcaaaggca   1260
ctcaacttta taaaccctga cgaactttca atgcagtgca ttttgatcgc attgaacagg   1320
tttcttcagg agaaacatgg ttcaaaaatg gcctttttag atggtaatcc tcctgagaga   1380
ctttgcatgc cgattgttga acacattgag tcaaaaggtg gccaagtcag actgaactca   1440
cgaataaaaa agattgagct gaatgaggat ggaagtgtca agagttttat actgagtgac   1500
ggtagtgcaa tcgagggaga tgcttttgtg tttgccgctc cagtggatat tttcaagctt   1560
ctattgcctg aagactggaa agagattcca tatttccaaa agttggagaa gttagtcgga   1620
gtacctgtga taaatgtaca tatatggttt gacagaaaac tgaagaacac atatgatcat   1680
ttgctcttca gcagaagctc actgctcagt gtgtatgctg acatgtctgt tacatgtaag   1740
gaatattaca accccaatca gtctatgttg gaattggttt ttgcacctgc agaagagtgg   1800
atatctcgca gcgactcaga aattattgat gcaacgatga aggaactagc aacgcttttt   1860
cctgatgaaa tttcagcaga tcaaagcaaa gcaaaaatat tgaagtacca tgttgtcaaa   1920
actccgaggt ctgtttataa aactgtgcca ggttgtgaac cctgtcggcc tttacaaaga   1980
tccccaatag aggggtttta tttagccggt gactacacga aacagaaata cttggcttca   2040
atggaaggcg ctgtcttatc aggaaagctt tgtgctcaag ctattgtaca ggattatgag   2100
ttacttgttg gacgtagcca aaagaagttg tcggaagcaa gcgtagttta gctttgtggt   2160
tattatttag cttctgtaca ctaaatttat gatgcaagaa gcgttgtaca caacatatag   2220
aagaagagtg cgaggtgaag caagtaggag aaatgttagg aaagctccta tacaaaagga   2280
tggcatgttg aagattagca tctttttaat cccaagttta aatataaagc atattttatg   2340
gaattc                                                              2346
```

-continued

<210> SEQ ID NO 4
<211> LENGTH: 151
<212> TYPE: DNA
<213> ORGANISM: Artificial
<220> FEATURE:
<223> OTHER INFORMATION: cDNA fragment of tobacco ribulose-biphosphate carboxylase/oxygenase small subuni

<400> SEQUENCE: 4

```
cctctgcagc agttgccacc cgcagcaatg ttgctcaagc taacatggtt gcacctttca     60

ctggccttaa gtcagctgcc tcattccctg tttcaaggaa gcaaaacctt gacatcactt    120

ccattgccag caacggcgga agagtgcaat g                                   151
```

<210> SEQ ID NO 5
<211> LENGTH: 200
<212> TYPE: DNA
<213> ORGANISM: Artificial
<220> FEATURE:
<223> OTHER INFORMATION: cDNA fragment of tobacco transketolase

<400> SEQUENCE: 5

```
cctacctaca cacctgaaag tccagcggat gccaccagaa acctgtccca acaaaacctg     60

aatgctcttg ccaaggttct tcctggtttc cttggtggta gtgctgatct tgcctcatca    120

aacatgaccc tcatgaaaat gtttggtgac ttccaaaaga acaccccaga ggagcgtaat    180

ctaaggtttg gtgttcgtga                                                200
```

<210> SEQ ID NO 6
<211> LENGTH: 842
<212> TYPE: DNA
<213> ORGANISM: Artificial
<220> FEATURE:
<223> OTHER INFORMATION: nucleotide sequence of the CaMV 35S promoter region

<400> SEQUENCE: 6

```
gcggccgcgt tcctacgcag caggtctcat caagacgatc tacccgagta acaatctcca     60

ggagatcaaa taccttccca agaaggttaa agatgcagtc aaaagattca ggactaattg    120

catcaagaac acagagaaag acatatttct caagatcaga agtactattc cagtatggac    180

gattcaaggc ttgcttcata aaccaaggca agtaatagag attggagtct ctaaaaaggt    240

agttcctact gaatctaagg ccatgcatgg agtctaagat tcaaatcgag gatctaacag    300

aactcgccgt gaagactggc gaacagttca tacagagtct tttacgactc aatgacaaga    360

agaaaatctt cgtcaacatg gtggagcacg acactctggt ctactccaaa aatgtcaaag    420

atacagtctc agaagaccaa agggctattg agacttttca acaaaggata atttcgggaa    480

acctcctcgg attccattgc ccagctatct gtcacttcat cgaaaggaca gtagaaaagg    540

aaggtggctc ctacaaatgc catcattgcg ataaaggaaa ggctatcatt caagatgcct    600

ctgccgacag tggtcccaaa gatggacccc cacccacgag gagcatcgtg gaaaaagaag    660

acgttccaac cacgtcttca aagcaagtgg attgatgtga catctccact gacgtaaggg    720

atgacgcaca atcccactat ccttcgcaag acccttcctc tatataagga agttcatttc    780

atttggagag gacacgctga aatcaccagt ctctctctat aaatctatct ctctctctat    840

aa                                                                   842
```

<210> SEQ ID NO 7
<211> LENGTH: 6355
<212> TYPE: DNA

-continued

<213> ORGANISM: Artificial
<220> FEATURE:
<223> OTHER INFORMATION: cDNA sequence of the genome of TMV-U2

<400> SEQUENCE: 7

```
gatgttttaa tagttttcga caacaacaat taaaacaaaa acaacatatt acaaacaaca     60
aacaacaaca atggcacaca tacaatctat aattagcaac gcccttcttg aaagcgtgag    120
tggtaaaaac actctcgtta atgaccttgc aagaaggcgc atgtacgata cggccgtgga    180
agaatttaac gcccgcgacc gtagaccaaa ggtcaacttt tccaaaacta ttagcgaaga    240
gcaaacgctt ctagtctcca acgcgtaccc ggagttccag attacctttt ataatactca    300
aaatgccgta cacagtttgg ctggaggttt gagagcatta gaattggaat atctgatgct    360
acaagttccc tatggatcgc cgacatatga tataggtggg aactttgcag cacatttgtt    420
caaaggcagg gattacgtgc attgctgtat gcccaatctg gacatacgag atataatgag    480
gcacgaagga caaaaggact caattgagat gtatttgtcc agattgtctc gttctaacaa    540
ggtaattcct gagtttcaaa gggaggcttt taacaggtat gcagaagctc ccaacgaagt    600
ctgctgctct aaaacttttc aggattgtcg aatacatccg ccagagaata gtggtagaag    660
atacgctgtt gctctgcaca gtttgtatga tattcctgtg catgagtttg gagctgcgtt    720
aatatctaag aatatacatg tatgttatgc agcttccatt ttggcagaag cattattact    780
agaccagacg gaggttacgc ttaatgaaat aggcgcaact ttcaaaagag aaggtgatga    840
tgtttctttt ttctttgctg atgaaagtac tttaaattat agtcataaat acaaaaatat    900
cttgcattat gtagttaaat cttactttcc tgcttctagt agaatagttt actttaagga    960
atttttagtc actagggtta atacttggtt ttgtaaattt accaaagtag atacctatat   1020
tctgtacaag agtgttagac aagtagggtg tgatagtgat cagttctatg aggcgatgga   1080
agacgccttt gcttacaaga aaaccttggc catgttcaac actgaaagag caatctttag   1140
agacacggct tcggttaact tttggttccc taagatgaag gacatggtga tagtaccgct   1200
gtttgagggt tctattacca gcaaaaagat gacaaggagt gaggtcattg ttaatcgtga   1260
cttcgtttac acagtgctta atcatatcag aacatatcaa gccaaagcgt taacttacca   1320
gaacgtatta tctttcgtgg agtctataag atcccgcgtg ataatcaatg gtgttactgc   1380
taggtctgaa tgggatgtag ataaagcaat tcttcaaccc ttgtcaatga ctttcttctt   1440
gcagactaag ctggctgcgc ttcaagacga tatagtaatg ggaaagtttc ggtgcttgga   1500
taagaccact tctgaactta tttgggatga ggtgggcaaa ttttttggaa acgttttccc   1560
cactatcaaa gagagattgg tgagcaggaa aattctggat gtaagtgaga atgctctgaa   1620
gatcaagatc ccagatctgt atgtcacatg gaaagacagg ttcgtagctg aatacaccaa   1680
gtctgaggag ttaccgcatc tagatatcaa gaaggactta gaagaagctg agcaaatgta   1740
cgacgcgtta tcagaattat ctatccttaa gggtgctgat aatttcgata tcgcgaagtt   1800
caaagacatg tgcaaggctt tagatgttag tcctgatgtg gcagcacgag taatcgttgc   1860
agtggccgag aatagaagcg gtttaactct tacttttgat aagccaaccg aggagaatgt   1920
ggctaaggct cttaaaagca cggcgtctga ggccgtggta tgtcttgaac cgacatccga   1980
agaggtgaac gtaaataaat tttctattgc tgagaaaggg agattgcctg tgtgtgcaga   2040
aagtcatggt ttgacgaatg ctaacttaga gcaccaggag ttggagtccc tcaacgattt   2100
ccataaggct tgcgtggata gtgtgattac aaagcaaatg gcatcggttg tctacactgg   2160
ctcactcaaa gttcaacaaa tgaagaacta tgtggacagt ttggcagctt cgttgtccgc   2220
```

-continued

```
cactgtatca aatctatgca agtcactaaa ggatgaagtc gggtatgatt ctgattccag   2280
ggagaaagtt ggtgtttggg atgtcacttt gaaaaagtgg ctcctcaaac ctgcggccaa   2340
aggtcattca tggggagttg tcctggatta caaggggaaa atgtttactg cacttctatc   2400
ttatgaagga gatagaatgg tgactgagag cgactggagg agggtggctg tatcatctga   2460
tacaatggta tattctgata ttgcaaagct ccaaaatctg aggaaaacaa tgagagacgg   2520
tgaaccccac gaacctactg caaagatggt acttgtggat ggggtgcctg gttgtggaaa   2580
gtacaaagga gattttgaaa gatttgatct tgatgaggat ttgatcttgg ttcctggaaa   2640
acaagctgct gctatgatca gaagaagggc taattcatct ggactgataa gagccacaat   2700
ggacaatgtg agaacggtag attcacttct aatgcatcca aaaccgcgat cacacaagag   2760
gctttttatt gatgaagggt tgatgctgca caccggttgt gttaacttcc tggtgcttat   2820
ctctggttgc gacatcgcat acatttacgg agatacacag cagattcctt tcattaacag   2880
agttcagaat ttcccgtatc ccaaacattt tgagaagctg caagtggatg aagttgagat   2940
gaggaggacc acactgagat gcccaggtga tgtgaatttt ttcctacaat cgaagtacga   3000
aggagcggtg acaaccactt caactgtaca acgatcggtc tcatctgaga tgataggcgg   3060
taagggagta ctaaacagtg tttccaaacc actaaaaggg aaaattgtaa ctttcactca   3120
ggctgataaa tttgagttag aggagaaggg ctataagaat gtgaacaccg ttcatgagat   3180
ccaaggagaa acctttgaag atgtgtcgct ggtcagattg acggcaactc cactgactct   3240
gatttccaag tcttccccgc atgttctagt cgctctgact agacacacaa agagcttcaa   3300
atattacacc gtagtgttag atcctttagt acagataatt agtgatttgt cttctttaag   3360
ctccttcctt ttagaaatgt atatggtaga agcaggtagt agatagcaat tacagatgga   3420
tgcagtgttc aaaggtcata atctctttgt ggcaacacct aaatcaggag actttccaga   3480
tctacagttc tattacgatg tatgcctccc tggtaatagt actatactta acaagtatga   3540
tgctgttacc atgaggttac gtgataatag tcttaatgtg aaggattgtg ttcttgattt   3600
ttccaaaagt attccgatgc caaaggaggt gaaaccatgt ctagagccag ttttgcgtac   3660
cgcggcggaa ccgccaaggg ctgcaggact actcgaaaat ctggttgcaa tgattaaaag   3720
aaatttcaac gcaccagacc tgacggggac gattgacatt gagagcaccg catctgttgt   3780
agtagataag tttttgata gctattttat taaaaaagaa aaatacacaa aaaatattgc   3840
tggagtgatg acgaaggatt caatgatgag atggttggaa aacaggaaag aagtactatt   3900
ggacgacttg gctaactaca attttacaga tctgccggcc atcgatcagt acaagcacat   3960
gatcaaggct caaccaaaac agaaattgga cctttcaatt cagaatgaat accctgctct   4020
gcaaacaatt gtctaccatt cgaagcagat caacggtatt ttggccggtt tctcagagct   4080
tacaaggttg ctgctcgagg catttgattc taagaagttt cttttcttta ctaggaaaac   4140
tccagaacag attcaagaat ttttctcgga tctcgactcg cacgttccta tggatgtgtt   4200
agaactggat atttctaagt atgataagtc acagaacgag tttcattgtg ctgtagagta   4260
tgaaatatgg aaaagattgg gtctcaatga gtttttggcc gaagtgtgga aacaagggca   4320
caggaaaaca actttgaagg attacattgc tggaatcaag acatgtctgt ggtatcaaag   4380
gaaaagcggt gatgtgacta ctttcatcgg caatactgtt ataatagcag cttgcttggg   4440
ttcaatgtta ccgatggaaa aggtcataaa aggtgctttt tgtggagacg attccgtttt   4500
gtattttcca aagggtttgg atttccctga cattcagtca tgtgctaatc tcatgtggaa   4560
```

-continued

```
ttttgaggcc aaactgtata gaaagaggta cggttacttt tgtggtagat acatcataca   4620

ccatgataag ggagcaatag tgtattatga tcctttgaag ttgatctcca aacttggggc   4680

aaaacatatc aaggattatg atcacttaga agagttaagg gtgtctttgt gcgatgttgc   4740

ttgttcgctc ggaaactggt gcttaggctt tccgcagctg aacgcagcta tcaaggaggt   4800

tcataaaacc gcgattgatg gttcgtttgc ttttaattgt gttaacaaat ttttgtgtga   4860

taaattttta tttagaactt tgtttttaaa tggctgttag tctcagagat actgtcaaaa   4920

ttagcgagtt cattgatctt tcgaaacagg atgagatact tccggcattc atgactaagg   4980

tcaagagtgt tagaatatcg actgtggaca agattatggc tgttaagaat gatagtcttt   5040

ctgatgtaga tttacttaaa ggtgttaagt tagttaagaa agggtatgtg tgcttagctg   5100

atttggtagt gtctggggag tggaatctcc cggataactg ccgtggtggt gtcagtgttt   5160

gtattgtaga taagagaatg aaaaggagta aggaagcaac gctgggtgcg tatcacgccc   5220

ctgcttgcaa aaagaatttt tcttttaagc taatccctaa ttattcaata acatccgagg   5280

atgctgagaa gcacccgtgg caagtgttag tgaatatcaa aggagtggct atggaagaag   5340

gatactgtcc tttatctttg gagttcgttt caatttgtgt agtacataaa aataatgtaa   5400

gaaaaggttt gagggaacgt attttgagtg tgacagacgg ctcgccaatt gaactcactg   5460

aaaaggttgt tgaggagttc gtggatgaag taccaatggc tgtgaaactc gaaaaggttc   5520

cggaaaacaa aaaagaaatg gtaggtaata atgttaataa taagaaaata aataacagtg   5580

gtaagaaggg ttttaaaatt gaggaaattg aggataatgt aagtgatgac gagtctatcg   5640

cgtcatcgag tacgttttaa tcaatatgcc ttatacaatc aactctccga gccaatttgt   5700

ttacttatct tccgcttacg cagatcctgt gcagctgatc aatctgtgta caaatgcatt   5760

gggtaaccag tttcaaacgc aacaagctag gacaacagtc caacagcaat ttgcggatgc   5820

ctggaaacct gtgcctagta tgacagtgag atttcctgca tcggatttct atgtgtatag   5880

atataattcg acgcttgatc cgttgatcac ggcgttatta aatagctttg atactagaaa   5940

tagaataata gaggttgata atcaacccgc accgaatact actgaaatcg ttaacgcgac   6000

tcagagggta gacgatgcta ctgtagctat aagggcttca atcaataatt tggctaatga   6060

actggttcgt ggaactggca tgttcaatca agcaggcttt gagactgcta gtggacttgt   6120

ctggaccaca actccggcta cttagctatt gttgtgagat ttcctaaaat aaagtcgctg   6180

aagacttaaa attcagggtg gctgatacca aaatcagcag tggttgttcg tccacttaaa   6240

tataacgatt gtcatatctg gatccaacag ttaaaccatg tgatggtgta tactgtggta   6300

tggcgtaaaa catcggagag gttcgaatcc tcccctaacc gccggtagcg gccca        6355
```

<210> SEQ ID NO 8
<211> LENGTH: 18
<212> TYPE: DNA
<213> ORGANISM: Artificial
<220> FEATURE:
<223> OTHER INFORMATION: nucleotide sequence of the T7 RNA polymerase promoter

<400> SEQUENCE: 8

```
taaacgactc actatagg                                                 18
```

<210> SEQ ID NO 9
<211> LENGTH: 22
<212> TYPE: DNA
<213> ORGANISM: Artificial
<220> FEATURE:

-continued

<223> OTHER INFORMATION: nucleotide sequence of the SP6 RNA polymerase promoter

<400> SEQUENCE: 9
atttaggtga cactatagaa ta 22

<210> SEQ ID NO 10
<211> LENGTH: 25
<212> TYPE: DNA
<213> ORGANISM: Artificial
<220> FEATURE:
<223> OTHER INFORMATION: polylinker sequence

<400> SEQUENCE: 10
tgcaggctaa tactagcggc cgcgt 25

<210> SEQ ID NO 11
<211> LENGTH: 207
<212> TYPE: DNA
<213> ORGANISM: Artificial
<220> FEATURE:
<223> OTHER INFORMATION: cDNA fragment of tobacco acetolactate synthase

<400> SEQUENCE: 11
cgatgggatt tggtttgccc gctgctattg gtgcggctgt tggaagacct gatgaagttg 60
tggttgacat tgatggtgat ggcagtttca tcatgaatgt gcaggagcta gcaactatta 120
aggtggagaa tctcccagtt aagattatgt tactgaataa tcaacacttg ggaatggtgg 180
ttcaatggga ggatcggttc tataagg 207

<210> SEQ ID NO 12
<211> LENGTH: 224
<212> TYPE: DNA
<213> ORGANISM: Artificial
<220> FEATURE:
<223> OTHER INFORMATION: cDNA fragment of tobacco cet-2 repressor of early flowering

<400> SEQUENCE: 12
gtctgatccc cttgtgattg gtagagtgat tggggaagtt gttgattatt tcactccaag 60
tgttaagatg tctgttactt ataacagcag caagcatgtt tataatgggc atgaactctt 120
tccttcctca gtcacctcta aacctagggt tgaagttcat ggaggtgatt tgagatcttt 180
ctttacaatg atcatgatag acccagatgt tcctggtcct agtg 224

<210> SEQ ID NO 13
<211> LENGTH: 195
<212> TYPE: DNA
<213> ORGANISM: Artificial
<220> FEATURE:
<223> OTHER INFORMATION: cDNA fragment of tobacco cellulose synthase cesA-1a

<400> SEQUENCE: 13
gttcctcaat ctgctacacc agagaccctt ttgaaagagg ctattcatgt tatcagttgt 60
ggttatgaag ataaatcaga atggggaagt gagattggat ggatctatgg ttctgtcaca 120
gaggatattc ttactggatt taagatgcat gcccgtggtt ggcgatctat atactgtatg 180
cccaagagac ctgcc 195

<210> SEQ ID NO 14
<211> LENGTH: 102
<212> TYPE: DNA

```
<213> ORGANISM: Artificial
<220> FEATURE:
<223> OTHER INFORMATION: cDNA fragment of Aequorea victoria enhanced
      green fluorescent protein

<400> SEQUENCE: 14

atcggcgtgg ctgctgtggc tgatgatcag aaacagcagc agggtgctca ccaggaagaa     60

gctgggcatc tggctgaaca ggaagaagcc catatagttt gc                       102


<210> SEQ ID NO 15
<211> LENGTH: 261
<212> TYPE: DNA
<213> ORGANISM: Artificial
<220> FEATURE:
<223> OTHER INFORMATION: 3' nontranslated sequence of the nopaline
      synthase gene

<400> SEQUENCE: 15

cgaagcagat cgttcaaaca tttggcaata aagtttctta agattgaatc ctgttgccgg     60

tcttgcgatg attatcatat aatttctgtt gaattacgtt aagcatgtaa taattaacat    120

gtaatgcatg acgttattta tgagatgggt ttttatgatt agagtcccgc aattatacat    180

ttaatacgcg atagaaaaca aaatatagcg cgcaaactag gataaattat cgcgcgcggt    240

gtcatctatg ttactagatc g                                              261


<210> SEQ ID NO 16
<211> LENGTH: 25
<212> TYPE: DNA
<213> ORGANISM: Artificial
<220> FEATURE:
<223> OTHER INFORMATION: Agrobacterium tumefaciens TL-DNA right
      border sequence

<400> SEQUENCE: 16

aattacaacg gtatatatcc tgcca                                           25


<210> SEQ ID NO 17
<211> LENGTH: 25
<212> TYPE: DNA
<213> ORGANISM: Artificial
<220> FEATURE:
<223> OTHER INFORMATION: Agrobacterium tumefaciens TL-DNA left border
      sequence

<400> SEQUENCE: 17

atttacaatt gaatatatcc tgccg                                           25


<210> SEQ ID NO 18
<211> LENGTH: 260
<212> TYPE: DNA
<213> ORGANISM: Artificial
<220> FEATURE:
<223> OTHER INFORMATION: cDNA fragment of tobacco cellulose synthase
      cesA-2

<400> SEQUENCE: 18

gaagcaatcc atgtcattag ctgtggttat gaagaccgaa gtgattgggg aagggagatt     60

gcttggatct acggttctgt tacggaagat attcttactg gtttcaagat gcatgcacgt    120

ggctggcggt caatctactg tatgcctaag cgaccacttt caagctctgc ccctatcaac    180

ctttcagatc gtctaaatca agtgcttcgg tgggcgcttg gttcagtgga aattcttttc    240

agtaggcatt gtcccatatg                                                260
```

METHODS AND MEANS FOR DELIVERING INHIBITORY RNA TO PLANTS AND APPLICATIONS THEREOF

CROSS-REFERENCE TO A RELATED APPLICATION

This application claims priority under 35 USC §119 to U.S. Provisional Application No. 60/340,488 entitled METHODS AND MEANS FOR DELIVERING INHIBITORY RNA TO PLANTS AND APPLICATIONS THEREOF, and filed on Dec. 18, 2001, the entire content of which is hereby incorporated by reference and relied upon in its entirety.

FIELD OF THE INVENTION

This invention relates to the field of functional genomics in plants. More particularly it relates to methods and means for modulating, reducing, or eliminating the expression of selected nucleic acids in plants. These methods and means may be used to determine or validate the function of isolated nucleic acid sequences in plants. Provided are viral vectors and viral vector kits, whereby one of the vectors is derived from a satellite virus and whereby said vector comprises the nucleotide sequence encoding the N-terminal amino acids of the satellite virus coat protein and a gene-silencing construct. Further provided are methods for obtaining an improved or enhanced gene-silencing phenotype.

BACKGROUND ART

The recent, rapid expansion of available nucleic acid sequence information has necessitated the development of methods for identifying the function of nucleic acid sequences, particularly transcribed nucleic acid sequences such as expressed sequence tags, with unknown function, in an efficient and labor-cost effective way.

To identify or validate the role of sequenced nucleic acids from plants of unknown or hypothetical function it is necessary to produce or identify plants in which those nucleic acids are either structurally or functionally inactivated. Plants wherein predetermined nucleic acid sequences are structurally inactivated can be generated using recombination technologies such as homologous recombination as described by Kempin et al. (1997). Alternatively, plants with a mutation in a predetermined nucleotide sequence can be identified by screening a saturated mutant library, such as but not limited to a T-DNA insertion library or a transposon insertion library (see e.g. Pereira and Aerts, 1998). These methodologies all require the generation of a large number of permanently altered plants, and thus are less amenable for application in high throughput methods. Moreover, the recovery of plants with recessive mutations in essential genes requires time-consuming breeding to maintain the plants in heterozygous state. Maintenance of dominant lethal mutations in essential genes is virtually impossible.

Plants with functionally inactivated predetermined nucleotide sequences can be generated in a straightforward way using methodologies wherein inhibitory RNA is generated, such as antisense or sense RNA.

The use of inhibitory RNA to reduce or abolish gene expression, also known as gene silencing, is well established in the art and is the subject of several reviews (e.g. Baulcombe 1996, Stam et al. 1997, Depicker and Van Montagu, 1997). Several patent applications relate to the practical exploitation of gene silencing.

U.S. Pat. No. 5,190,931 and EP 0 467 349 A1 describe methods and means to regulate or inhibit gene expression in a cell. These comprise incorporating into or associating with the genetic material of the cell a non-native nucleic acid sequence which is transcribed to produce an mRNA which is complementary to and capable of binding to the mRNA produced by the genetic material of that cell.

EP 0 240 208 describes a method to regulate expression of genes encoded for in plant cell genomes. This method is achieved by integration of a gene under the transcriptional control of a promoter which is functional in the host and in which the transcribed strand of DNA is complementary to the strand of DNA that is transcribed from the endogenous gene(s) one wishes to regulate.

EP 0 223 399 A1 describes methods to effect useful somatic changes in plants by causing the transcription in the plant cells of negative RNA strands which are substantially complementary to a target RNA strand. The target RNA strand can be a mRNA transcript created in gene expression, a viral RNA, or other RNA present in the plant cells. The negative RNA strand is complementary to at least a portion of the target RNA strand to inhibit its activity in vivo.

EP 0 647 715 A1 and U.S. Pat. Nos. 5,034,323, 5,231,020 and 5,283,184 describe methods and means for producing plants exhibiting desired phenotypic traits, by selecting transgenes that comprise a DNA segment operably linked to a promoter, wherein transcription products of the segment are substantially homologous to corresponding transcripts of endogenous genes, particularly endogenous flavonoid biosynthetic pathway genes.

W0 93/23551 describes methods and means for the inhibition of two or more target genes. These methods comprise introducing into the plant a single control gene, which has distinct DNA regions homologous to each of the target genes, and a promoter operative in plants adapted to transcribe from such distinct regions RNA that inhibits expression of each of the target genes.

A major disadvantage of these technologies, which hampers the exploitation thereof in high throughput gene function discovery methods, is the intrinsic unpredictability and low occurrence of the gene silencing phenomenon.

Recently, Waterhouse et al. (1998) and WO99/53050 have described methods and means to make gene silencing in plants more efficient and predictable, by simultaneous expression of both sense and antisense constructs in cells of one plant. The sense and antisense nucleic acids may be in the same transcriptional unit, so that a single RNA transcript that has self-complementarity is generated upon transcription.

Hamilton et al. (1998) describe improved silencing e.g. of tomato ACC-oxidase gene expression using a sense RNA containing two additional upstream inverted copies of its 5' untranslated region.

WO 98/53083 describes constructs and methods for enhancing the inhibition of a target gene within an organism, involving the insertion into the gene silencing vector of an inverted repeat of all or part of a polynucleotide region within the vector.

WO01/12824 describes a method and means of reducing the expression of a target nucleic acid, and thereby altering the phenotype of an organism, especially a plant, by providing aberrant, target specific RNA to the nucleus of the host cell. The method involves chimeric constructs comprising a promoter, a DNA region encoding the target RNA, a self-splicing ribozyme and a 3'end.

It should be clear however, that the use of inhibitory RNA as a tool in reversed genetics analysis of gene function via high throughput methods, whereby the inhibitory RNA is generated from gene-silencing constructs which are stably integrated in the genome of transgenic plants, suffers from the same drawbacks as mentioned herein above.

EP 0 194 809 and U.S. Pat. No. 5,500,360 suggest the use of viral RNA vectors to produce regulatory RNA such as anti-sense RNA.

Initial exploration of the use of viral vectors to deliver inhibitory RNA into cells of plants has been described by Chapman (1991). In this publication, gene silencing constructs comprising nucleotide sequences complementary to the translated region of the GUS gene on a PVX derived viral vector were described. The experiments however, remained inconclusive as to whether gene silencing could be provoked using viral vectors for the production of inhibitory RNA.

WO 93/03161 is directed toward recombinant plant viral nucleic acids and to hosts infected thereby. The non-native nucleic acid sequence which is transcribed may be transcribed as an RNA which is capable of regulating the expression of a phenotypic trait by an anti-sense mechanism.

English et al., 1996 describe the suppression of the accumulation of a viral vector comprising a foreign nucleotide sequence in transgenic plants exhibiting silencing of nuclear genes comprising the same foreign nucleotide sequences, thus linking gene silencing and viral vectors, albeit in a reverse way as envisioned here.

Kumagai et al. (1995) described the inhibition of phytoene desaturase gene by viral delivery of antisense and sense RNA.

WO 95/34668 suggests the use of genetic constructs based on RNA viruses which replicate in the cytoplasm of cells to provide inhibitory RNA, either antisense or co-suppressor (sense) RNA.

Baulcombe et al. (1998) and Ruiz et al. (1998) describe virus-induced gene silencing of the endogenous phytoene desaturase gene (PDS) or of a green fluorescent protein transgene (GFP) in plants, using potato virus X derived vectors carrying inserts homologous to PDS and GFP, respectively. The authors further suggested that virus-induced gene silencing may develop into a novel assay of gene function, by introducing a fragment of the genome into a viral vector and inferring the function of the gene from the symptoms of the infected plants exhibiting gene silencing.

WO90/12107 describes the use of STMV vectors for the making of desired proteins in plant cells by replacing the STMV coat protein gene with a heterologous nucleotide sequence, but the use of satellite viruses for introduction of inhibitory RNA is not described.

WO0063397 describes a method for virus-induced gene silencing of endogenous genes or transgenes that makes use of a two component system made up of a satellite RNA virus vector and its corresponding helper virus.

The prior art methods based on plant viral RNA vectors described above still suffer from the following drawbacks:

- the phenotype induced by the inhibitory RNA may often be weak or very weak
- the phenotypic pattern induced by the inhibitory RNA may not be uniform throughout the plant tissue and may be present in a patchy or mosaic pattern
- the phenotype induced by the inhibitory RNA may often be masked by symptoms caused by the virus
- interpretation of the gene silencing phenotype may be hampered by intra- and inter-experimental variation
- in known gene-silencing systems the silencing of genes expressed in meristematic tissues was often not possible, due to an inability of the vector or signal to enter meristems
- in known gene-silencing systems, with the exception of WO0063397, the chimeric viral vectors carrying gene-silencing sequences often were themselves targets of silencing, compromising the effectiveness.

These and other problems have been solved as described hereinafter, including the different embodiments described in the claims.

SUMMARY OF THE INVENTION

The invention provides methods, vectors and kits for introducing inhibitory RNA into plant cells.

The invention provides viral RNA vectors derived from satellite viruses, particularly derived from satellite tobacco mosaic virus. These vectors comprise the nucleotide sequence normally encoding the N-terminal amino acids of the coat protein of the satellite virus, a short fragment of at least 10 contiguous nucleotides of the nucleotides at position 1365 to position 1394 of SEQ ID No 3 and one or more gene-silencing constructs. These vectors can replicate and spread systemically and can induce a gene-silencing phenotype which is stronger and more reproducible than when viral RNA vectors previously described in the art are used.

A further objective of the invention is to provide methods for introducing inhibitory RNA into plant cells. The methods comprise providing a viral RNA vector, which is derived from a satellite RNA virus and infecting a plant with the viral RNA vector and a corresponding helper virus. The viral RNA vector is characterized in that it is derived from a satellite RNA virus and in that it comprises a nucleotide sequence encoding the N-terminal amino acids of the satellite virus coat protein, a stretch of at least 10 contiguous nucleotides of nucleotides 1365 to 1394 of SEQ ID No 3, and a gene-silencing construct. In one embodiment the gene-silencing construct comprises a nucleotide sequence of at least 27 nucleotides in length, wherein the 27 nucleotides have at least 75% sequence identity to the target gene within the plant cell. The gene-silencing constructs comprised within the viral RNA vector may comprise antisense RNA or sense RNA. Further, the inhibitory RNA may comprise an inverted repeat. The target gene within the plant cell may be an endogenous gene or a transgene. In another embodiment, the nucleotide sequence encoding the N-terminal amino acids of the satellite virus coat protein comprises nucleotides 162 to 328 of SEQ ID No 1. In a further embodiment, the short stretch of contiguous nucleotide of nucleotides 1365 to 1394 of SEQ ID NO 3 comprises 10, 21, 22, 27 or 30 contiguous nucleotides. In still a further embodiment, the viral RNA vector is derived from satellite tobacco mosaic virus (STMV).

In another embodiment of the invention viral RNA vectors for introducing inhibitory RNA into a plant cell are provided. The viral RNA vector may be derived from an icosahedral satellite virus, wherein the virus comprises a nucleotide sequence encoding a satellite virus coat protein, such as STMV. The viral RNA vectors comprise a nucleotide sequence encoding the N-terminal amino acids of a satellite virus coat protein and a nucleotide sequence comprising at least 10 contiguous nucleotides of nucleotides 1365 to 1394 of SEQ ID No 3. A polylinker sequence may be comprised downstream (3') of the stretch of 10 contiguous nucleotides. In a further embodiment cDNA copies of the viral RNA vectors are provided. The viral RNA vectors may further comprise a gene-silencing construct. In one embodiment the gene-silencing construct comprises about 50 to 250 nucleotides.

The invention further provides a kit for introduction of inhibitory RNA, preferably sense or antisense RNA or inhibitory RNA comprising an inverted repeat, into the cytoplasm of a plant cell. The kit comprises a viral RNA vector and a corresponding helper virus. The viral RNA vector is characterized in that it is derived from a satellite virus, and it comprises a nucleotide sequence encoding the N-terminal amino acids of the coat protein of the satellite virus and a sequence comprising at least 10 contiguous nucleotides of nucleotides 1365 to 1394 of SEQ ID No 3.

Also provided are methods by which the gene-silencing phenotype obtained can be enhanced or improved compared to methods known in the art. These methods comprise one or a combination of the following:

- co-inoculating a plant with a viral RNA vector and helper virus, incubating the plant for a time period sufficiently long to allow establishment of the viral RNA vector, removing the apical meristem of the plant, and identifying, amongst newly developed secondary tissue, tissue with an altered phenotype;
- providing to the plant tissue an *Agrobacterium* strain comprising a viral RNA vector as a cDNA copy, transcribed from a promoter and operably linked to T-DNA border sequences.

The first of these two methods is useful for further enhancing the gene-silencing phenotype of a plant. The second method is suited for improving the gene-silencing phenotype of a plant.

DETAILED DESCRIPTION OF THE EMBODIMENTS

It was found by the inventors that satellite viral RNA vectors comprising a frameshift mutation in the nucleotide sequence encoding the coat protein of the satellite virus, were able to replicate and spread systemically with high efficiency in plant tissue co-inoculated with the corresponding helper virus. Similar satellite viral RNA vectors comprising various sizes of deletions of the nucleotide sequence encoding the central amino acids of the coat protein had a strongly reduced capability to replicate and spread in planta. The presence of the complete, but due to the frameshift mutation non-functional, nucleotide sequence normally encoding the satellite virus coat protein seemed thus favorable over satellite viral RNA vectors where parts of this sequence were deleted. The above mentioned frameshift mutation was located downstream of the nucleotide sequence normally encoding the N-terminal amino acids of the satellite virus coat protein. Elaborating on this finding, gene-silencing sequences were inserted into the satellite viral RNA vector following the nucleotide sequence encoding the N-terminal amino acids of the coat protein (e.g. at the AgeI restriction site of the nucleotide sequence encoding the satellite virus coat protein of STMV). These sequences were found not to compromise the ability of the viral vector to replicate and spread systemically in planta and induce gene-silencing of the target genes.

A further unexpected finding was, that additionally the presence or absence in the satellite viral RNA vector of a short stretch of contiguous nucleotides of nucleotides 1365 to 1394 of SEQ ID No 3 determined the ability of the vector to induce efficient gene-silencing of target genes in plants. Vectors lacking the short stretch of contiguous nucleotides of nucleotides 1365 to 1394 of SEQ ID No 3 were not able to induce gene-silencing. Thus, vectors comprising the nucleotide sequence encoding the N-terminal amino acids of the satellite virus coat protein, a short stretch of contiguous nucleotides of nucleotides 1365 to 1394 of SEQ ID No 3 and a gene-silencing construct were found to be very effective tools for gene-silencing. In addition, in vectors with this configuration the nucleotide sequence encoding the central part of the satellite virus coat protein (nucleotides 329 to 600 of SEQ ID No 1) could surprisingly be deleted without compromising the ability of the viral vectors to replicate and spread and their usefulness as a tool for gene-silencing methods.

Without intending to limit the scope of the invention to a particular mode of action, it is thought that the presence of the short stretch of at least 10 contiguous nucleotides between the nucleotide sequence encoding the N-terminal amino acids of the coat protein and the gene-silencing construct may cause the inhibitory RNA to fold into a preferred, maybe particularly stable, secondary or tertiary RNA structure.

In one embodiment of the invention a method is provided to introduce inhibitory RNA for specific target gene(s) into a plant cell. The method comprises providing a viral RNA vector, which is derived from a satellite RNA virus and co-infecting a plant with the vector and its corresponding helper virus.

The vector is characterized in that it comprises the nucleotide sequence encoding the N-terminal amino acids of the satellite virus coat protein, a nucleotide sequence comprising at least 10 contiguous nucleotides of nucleotides 1365 to 1394 of SEQ ID No 3 and a gene-silencing construct. Preferably, the at least 10 contiguous nucleotides of nucleotides 1365 to 1394 of SEQ ID No 3 are downstream of the nucleotide sequence encoding the N-terminal amino acids of the satellite virus coat protein and the gene-silencing construct is preferably downstream of the at least 10 contiguous nucleotides of nucleotides 1365 to 1394 of SEQ ID No 3.

As used herein, “a satellite virus” indicates an RNA virus, preferably a single stranded RNA virus, the RNA genome of which is capable of replicating in a plant cell and being encapsidated by coat protein molecules to form a virus particle or virion, only when provided externally with any number of required essential functions therefor. By “externally provided” is meant that such functions are either not encoded by the satellite viral genome or that the transcription/translation product is non-functional. Satellite viruses thus depend upon external provision of essential functions, and may lack the capacity to encode functional replicase, movement protein, or other essential functions required to complete their life cycle inside a plant cell. In a natural situation, such essential functions are usually provided by an autonomously replicating virus or so-called “helper virus”.

The satellite virus genome normally comprises a nucleotide sequence encoding its coat protein and a “satellite RNA virus, wherein the virus comprises a nucleotide sequence encoding a coat protein” is used to mean a satellite RNA virus, the genome of which encodes the coat protein of this satellite RNA virus. Upon co-infection of a plant with the satellite RNA virus and a corresponding helper virus, the satellite virus coat protein would normally have the capability to encapsidate the satellite virus genome.

Satellite viruses useful for the present invention are well known in the art and include any satellite virus falling under the definition above, such as but not limited to satellite tobacco mosaic virus (STMV), satellite tobacco necrosis virus (STNV) or satellite maize white line mosaic virus. Satellite viruses useful for the present invention may include wild type isolates, but also encompassed by this definition are variants which result in reduced or minimal symptoms when infected on a host plant, particularly when co-inoculated with a corresponding helper virus. The definition also includes synthetic satellite viruses such as mutant viruses and chimeric satellite viruses.

A “viral RNA vector derived from a satellite RNA virus” should at least include cis elements from a satellite virus which are recognized by an externally provided replicase.

Further, RNA vectors according to the invention comprise the nucleotide sequence encoding the N-terminal amino acids of the satellite virus coat protein or a sequence essentially similar thereto. As used herein the "nucleotide sequence encoding the N-terminal amino acids of the coat protein" is to be interpreted as the nucleotide sequence of a satellite virus which, when transcribed and translated yields the N-terminal amino acids of the mature coat protein. In particular, if the amino acids making up the complete coat protein are equally divided into N-terminal, central- and C-terminal amino acids, the N-terminal amino acids comprise the N-terminal third of all amino acids. Due to the redundancy of the genetic code, this definition comprises various nucleotide sequences which yield the same amino acid sequence if they were to be translated.

This is not to be interpreted to mean that the viral RNA vector may not comprise a nucleotide sequence essentially similar to the nucleotide sequence normally encoding the complete coat protein, if the essentially similar sequence does not encode a functional coat protein. In the viral RNA vector, this essentially similar nucleotide sequence is non-functional, for example due to the presence of the short stretch of nucleotides 11365 to 1394 of SEQ ID No 3 between the nucleotides normally encoding the N-terminal amino acids and the nucleotides normally encoding the central and C-terminal amino acids of the coat protein.

The nucleotide sequence comprising the N-terminal amino acids of a coat protein may be either derived from a wild type satellite virus, particularly from STMV, or natural variants or strains thereof, or it may be synthetic. It may also comprise modifications, such as nucleotide changes, deletions or insertions.

The viral RNA vector of the method of the invention further comprises at least 10 contiguous nucleotides of the nucleotides 1365 to 1394 of SEQ ID No 3. This sequence may either be a synthetic sequence, or derived from nucleotide sequences encoding a phytoene desaturase, such as but not limited to tobacco or tomato phytoene desaturase. It is preferred that these at least 10 contiguous nucleotides are comprised downstream of (i.e. they are 3' to) the nucleotide sequence encoding the N-terminal amino acids of the coat protein.

Particularly suited for the invention are vectors comprising at least the 10 nucleotides 1365 to 1374 of SEQ ID No 3, the 21 nucleotides 1365 to 1385 of SEQ ID No 3, the 22 nucleotides 1365 to 1386 of SEQ ID No 3, or the 27 nucleotides 1365 to 1391 of SEQ ID NO 3.

Conveniently, the viral RNA vector comprises a number of unique or low-occurrence restriction recognition sites, such as provided by a polylinker having a nucleotide sequence, such as but not limited to SEQ ID No 10. One embodiment of the invention comprises so-called 'basic' viral RNA vectors into which a gene-silencing construct may be inserted, comprising a polylinker sequence downstream of the contiguous stretch of at least 10 contiguous nucleotides of nucleotides 1365 to 1391 of SEQ ID No 3. Conveniently a gene-silencing construct may be inserted into the polylinker sequence. Particularly suited for the invention are viral RNA vectors derived from STMV. Non-limiting examples of viral RNA vectors, suitable for the invention are described hereinafter. In the non-limiting examples two such 'basic' vectors are pVE349 and pVE350. Vectors derived from these basic vectors following insertion of a gene-silencing construct into the polylinker sequence are indicated by the superscript bv349 or bv350, respectively.

The invention also aims at providing the herein described viral RNA vectors. It is also an object of the invention to provide the viral RNA vectors described without the gene-silencing constructs or inhibitory RNA as well as their cDNA copies. In such vectors, the cDNA copies are under control of a promoter (which can be used in in vitro transcription methods available in the art) such as but not limited to the promoters recognized by single subunit bacteriophage polymerase promoters (T7, T3, SP6 RNA polymerase specific promoters and the like). A T7 RNA polymerase promoter useful for the invention may be that of SEQ ID No 8 or those known in the art, such as described in U.S. Pat. No. 476,072.

The viral RNA vector used in the methods of the invention may further comprise a gene-silencing construct.

"Gene-silencing constructs" as used herein is a nucleic acid, which by itself or when replicated or transcribed represent or yields "inhibitory RNA" comprising or consisting of sense RNA or antisense RNA, or a combination of both, comprising a nucleotide sequence which has at least 75%, preferably at least 80%, particularly at least 85%, more particularly at least 90%, especially at least 95% sequence identity with or is identical to the nucleotide sequence whose expression is to be suppressed, or its complement. Further, the nucleotide sequence of the sense or antisense region should preferably be at least about 19, 20 or 21 nucleotides, more preferably at least 27 nucleotides, more preferably at least 50 nucleotides, more preferably at least 100 nucleotides in length, more preferably at least about 250 nucleotides, particularly at least about 500 nucleotides but may extend to the full length of the transcribed region of the gene whose expression is to be reduced. The gene-silencing construct may be identical in sequence and length to the target nucleic acids, or they may be exactly complementary in sequence and identical in length to the target nucleic acids.

In one embodiment of the invention gene-silencing constructs of less than about 300 nucleotides are used, as longer gene-silencing constructs may result in lower levels of accumulated viral RNA and lower efficiency of gene silencing.

It is clear for the person skilled in the art that the gene-silencing constructs may comprise at the same time sense and anti-sense RNA targeted towards the same nucleotide sequence whose expression is to be reduced. The sense and antisense RNA may be at least partly complementary to each other and capable of forming a stem-loop structure. Such a configuration has been shown to increase the efficiency of gene-silencing, both in occurrence and level of gene-silencing (Waterhouse et al. 1998). It is also within the realm of the invention that "a vector comprising a gene-silencing construct" may comprise more than one gene-silencing construct, and that several target gene(s) or gene-families may be silenced as a result of carrying out the method of the invention with such vector. In certain situations this may be desirable. For example, the function of two nucleotide sequences may be known, but not their combined function and the phenotype (such as but not limited to, for example, the accumulation of certain metabolic intermediates) of the plant resulting from silencing of both concomitantly. This may for example be the situation for biosynthetic enzymes of a certain pathway. When several gene-silencing constructs are combined in one vector, the gene-silencing constructs may be arranged in tandem or may be inserted into one another.

It is equal whether the sequence identity of the gene-silencing construct with the sequence in the plant whose expression is to be suppressed is within a coding or non-coding region of the sequence in the plant whose expression is to be suppressed. It is also equal, whether the gene-silencing construct is inserted "in-frame" or not in frame into the viral RNA vector. "In-frame" as used herein means that, if the gene-silencing construct were to be translated, the resulting amino acid sequence of the gene-silencing construct would be identical to the corresponding sequence of the target gene.

As used herein the terms “gene-silencing” or “inhibitory” are not to be interpreted as meaning a complete abolishing of the expression of the target gene(s). Instead, these terms are intended to include any reduction in expression, measured either as a reduction in transcription and/or translation, as a reduction in the accumulation of transcripts or translation products such as proteins, or as a modification of the plant phenotype.

As used herein “phenotype” refers to any quantitative or qualitative characteristic of a plant, be it morphological (including macroscopic and microscopic characteristics), biochemical (including the presence, absence, or concentration of particular metabolites or molecules, such as mRNA or protein), functional or other.

The gene silencing phenotype generally persists over many weeks and silenced plants can in some instances even be kept for 6 months and longer (e.g. especially where silenced plants showed stunted growth and grow very slowly). This provides the possibility of analyzing plants not only macroscopically, but also microscopically or at a molecular and biochemical level. For example changes in metabolites, proteins, DNA or RNA levels, etc can be analyzed. Also, the response to external stimuli, such as changes in pathogen resistance/sensitivity, light sensitivity, heat or cold stress sensitivity, and the like, can be analyzed.

“Target gene” as used herein is the gene(s) of the plant which is/are to be silenced. As gene families may be silenced, the definition includes one or more endogenous genes or one or more chimeric genes (transgenes) or a combination of both.

In the non-limiting examples described hereinafter, using the methods and vectors of the invention, the following gene-silencing phenotypes were assessed macroscopically in co-inoculated tobacco plants (*Nicotiana tabacum*):

| Target gene(s) | Assessed gene-silencing phenotype |
|---|---|
| Phytoene desaturase (pds) | “Bleaching”, or “photobleaching” refers to the white phenotype of tissue, which develops when the enzyme phytoene desaturase, which is part of the carotenoid biosynthetic pathway, is rendered non-functional. A bleached phenotype can be obtained following treatment of tissue with the herbicide nonflurazon, a non-competitive inhibitor of pds (Kumagai et al. 1995). As a consequence of herbicide treatment, there is a dramatic decrease in carotenoids and chlorophylls, while phytoene accumulates. The reduction of the photoprotective carotenoids may lead to a rapid destruction of chlorophylls by photooxidation (the tissue becomes white). |
| Rubisco small subunit (rbcS) | “Chlorosis” refers to the pale-green discoloration of photosynthetically active tissue, following silencing of rbcS, compared to the deep-green color of non-silenced tissue. Plants showed stunted growth. |
| transketolase (tk) | “Yellow-red discoloration” refers to the phenotypic pale, yellow-red discoloration of tissue in which transketolase is silenced, described by Henkes et al. (2001) in tobacco transformed with an antisense transketolase construct. |
| acetolactate synthase (als) | “Leaf distortion and pigment deregulation” refers to the leaf deformation (crinkling and development of deep kerfs) seen in newly emerging leaves and the light- green/dark-green variegation seen in leaves of als silenced plants. |

-continued

| Target gene(s) | Assessed gene-silencing phenotype |
|---|---|
| cet-2 “repressor of early flowering” | “Early flowering” refers to an earlier occurrence of the shift from vegetative phase to reproductive phase (flower induction) in the gene-silenced plants compared to non-silenced plants. |
| cellulose synthase (cesA-1a & cesA-2) | “Leaf distortion and chlorosis” refers to the deformations, discoloration and changes in surface texture (surface lumps) seen in cellulose synthase silenced plants. |
| egfp and phytoene desaturase (pds) | “Bleaching” and “loss of green fluorescence” refers to the combined gene-silencing phenotype of “bleaching” (as described above for pds) and the loss of green fluorescence observed in 35S-egfp plants as a result of transgene silencing. |
| Chalcone synthase A (chsA) | “Chlorosis” refers to discoloration of leaf tissue; “variegated petals” refers to flower petals with different colored sectors (e.g. pink and white sectors) seen in silenced plants |
| Protoporphyrin oxidase (ppx-1) | “Chlorosis and necrosis” refers to discoloration of leaf tissue and necrotic spots, as well as small holes, on leaves |
| Glutamine synthase (gln 1-5) | “Chlorosis and necrosis” refers to pale green discoloration of leaf tissue and vascular necrosis |
| RNA polymerase II (rpII-a) | “white and severely deformed” refers to bleaching of leaf tissue and severe deformations of the silenced plants (e.g. very small leaves, no stem formation etc.) |
| Catalase 1 (cat-1) | “chlorotic spots” refers to discolored spots on leaves |
| Protein kinase 1 (npk-1) | “chlorotic spots” refers to discolored spots on leaves |
| Poly ADP-ribose polymerase (parp) | “chlorotic spots” refers to discolored spots on leaves |

The non-limiting examples showed that the vectors and methods of the invention are useful for introducing inhibitory RNA into cells and inducing strong and reproducible gene-silencing phenotypes in various plant tissues (such as, but not limited to, leaves, flowers and meristematic cells), both for one or more endogenous target genes, for one or more transgenes, or a combination of both. Silencing of rbcS exemplifies the silencing of a multigene family, while silencing of pds and egfp, using a single viral RNA vector, exemplifies the insertion of several gene-silencing constructs into a single vector, whereby several different target genes can be effectively silenced concomitantly. In addition it was shown that genes expressed in meristematic cells, such as but not limited to cet-2, can be silenced using the vectors and methods of the invention. Thus, the vectors of the invention are able to reach meristematic cells and may be used to silence genes required for meristematic identity and early leaf and flower development. This is an advantage over previously described viral RNA vectors, such as PVX, which are not able to enter meristematic cells.

In one embodiment of the invention, the vectors and methods are used to silence at least two endogenous target genes (or gene families). Gene silencing constructs of two target genes may be inserted into a single vector. Silenced plants can be scored for a combined (or “double”) knock-out phenotype. For example, a vector may comprise a chalcone synthase and a transketolase gene-silencing construct inserted into the polylinker region of the basic vectors. Preferably, the combined gene-silencing construct is no longer than about 300 nucleotides. For example, two gene-silencing constructs of about 50 to 150 nucleotides each may be inserted (in either sense or antisense orientation) into the polylinker region of the basic vectors of the invention.

In another embodiment of the invention tissue- or organ specific (or preferred) genes are silenced. A gene-silencing construct of a gene preferentially expressed in a certain tissue or organ, such as for example roots, leaves, flowers or stem, is inserted into the vector and in-vitro transcripts are co-inoculated onto tobacco leaves. A vector comprising chalcone synthase as target gene, will, for example, lead to a flower phenotype (variegated petals). Similarly, genes preferentially expressed in root tissue may be silenced using the vectors of the invention.

"A corresponding helper virus" as used herein, indicates those RNA viruses, preferably single stranded RNA viruses, which can supply the satellite virus or the derived viral RNA vector with the functions required in trans by that satellite virus or the derived viral RNA vector, to allow it to replicate in the cytoplasm of plant cells, and spread throughout an infected plant. Typically, corresponding helper viruses will provide the satellite virus or the vector derived thereof with a replicase (RNA dependent RNA polymerase) which recognizes the cis sequences present on the satellite virus RNA, and will allow replication of the satellite virus genome or the derived vector. Other proteins which may typically be provided by the helper virus are movement proteins, allowing inter alia, the plasmodesmata-mediated spread of viral particles from cell to cell. For satellite viruses or viral RNA vectors derived thereof which lack a functional coat protein encoding gene, corresponding helper viruses may also provide a functional coat protein. Preferably, the corresponding helper virus will be capable of autonomous systemic spread in an infected plant. However, such a systemic spread seems not to be a prerequisite for gene silencing. Functions required in trans for one particular viral RNA vector may be supplied in trans by different corresponding helper viruses.

It is clear that the corresponding helper viruses may be wild type isolates of RNA viruses, preferably single-stranded RNA viruses such as the tobamoviruses. Particularly preferred are rod-shaped RNA viruses such as tobamoviruses including tobacco mosaic virus (such as TMV strains U1, U2 U5), tomato mosaic virus, green tomato a typical mosaic virus, pepper mild mottle virus and odontoglossum ringspot virus. A preferred helper virus is tobacco mild green mosaic virus, such as for example TMV-U2 (SEQ ID No 7).

Also encompassed by the methods and means of the invention are variants of such wild type isolates, preferably variants or mutants which develop minimal symptoms when inoculated on host plants or when co-infected with a corresponding satellite virus or RNA vector derived thereof. Further preferred helper viruses may be variants or mutants of wild type isolates which have an extended host range such as tobamoviruses which can replicate and spread in corn or Brassicae.

Alternatively, the required functions in trans for the replication and movement of the viral RNA vector may be provided from the expression of chimeric genes, encoding proteins which can provide the required functions, integrated in the genome of the test plants.

Another objective of the invention is to provide kits for introducing inhibitory RNA into plant cells. Preferred kits to deliver inhibitory RNA or gene-silencing constructs to plant cells comprise a viral RNA vector derived from a satellite RNA virus, particularly from satellite tobacco mosaic virus (STMV), and a corresponding helper virus, particularly a rod-shaped corresponding helper virus, wherein the viral RNA vector comprises the nucleotide sequence encoding the N-terminal amino acids of the satellite virus coat protein, and a sequence comprising at least 10 contiguous nucleotides of nucleotides 1365 to 1394 of SEQ ID No 3. The nucleotide sequence comprising 10 contiguous nucleotides of nucleotides 1365 to 1394 is preferably located downstream of the nucleotide sequence encoding the N-terminal amino acids of the satellite virus coat protein or it is located between this sequence and a polylinker sequence. The kits of the invention may comprise any of the satellite viral RNA vectors of the invention described herein.

In another embodiment the kit comprises a viral RNA vector derived from satellite tobacco mosaic virus, preferably comprising the cis-elements required for replication, particularly comprising nucleotides 162 to 328 of SEQ ID No 1 and at least 10 contiguous nucleotides of nucleotides 1365 to 1394 of SEQ ID No 3.

In a further embodiment kits comprising a helper virus and one or more of the 'basic' satellite viral RNA vectors, or cDNA copies thereof, described hereinabove are provided, wherein gene-silencing constructs can easily be inserted into the polylinker sequence. Non-limiting examples of basic satellite RNA vectors are pVE349 and pVE350, and modifications thereof, such as, but not limited to, pVE359 and pVE360.

It is also an object of the invention to provide the kits comprising the helper viruses and satellite viral RNA vectors described, wherein the viral RNA vectors do not comprise a gene-silencing construct or inhibitory RNA, such as, but not limited to, the 'basic vectors' described elsewhere.

The viral RNA vectors and/or the corresponding helper virus may be provided as their respective cDNA copies, whereby the cDNA copies are under control of a promoter (which can be used in in vitro transcription methods available in the art) such as but not limited to the promoters recognized by single subunit bacteriophage polymerase promoters (T7, T3, SP6 RNA polymerase specific promoters and the like). The helper virus may also be provided as virus particles or solutions comprising virus particles, such as for example leaf-extracts from co-infected tissue. Such leaf extracts can be prepared as known in the art, for example, by grinding co-infected leaf tissue in 0.2M sodium-phosphate buffer (pH 7).

It will be clear to the person skilled in the art that viral RNA vectors may be generated conveniently by in vitro transcription methods from cDNA copies of the viral RNA. Likewise, infectious viral RNA for the corresponding helper viruses may be generated from cDNA copies of their genome. Viral vectors and corresponding helper viruses may also be maintained by replication in plant cells.

While the sequences in the sequence listing refer to DNA molecules, it is clear that, when it is stated in the description or the claims that a vector or nucleotide sequence comprises a nucleotide sequence as in the sequence listing, while it is clear that reference is made to an RNA molecule, the actual base-sequence of the RNA molecule is identical to the base-sequence of the sequence listing, with the difference that the T (thymine) is replaced by the U (uracil).

Methods to infect or inoculate plants and plant cells with viral RNA vectors, and helper viruses are well within in the realm of the person skilled in the art and may be performed according to the methods described in Walkey (1985). It should be clear that whenever it is stated that plants are co-infected or co-inoculated with a viral RNA vector and a corresponding helper virus, it is equal whether the helper virus is inoculated before, after or simultaneous with the viral RNA vector, provided however that there is a reasonable time limit between infection of the viral RNA vector or the corresponding helper virus.

In one embodiment of the methods of the invention, plants are co-inoculated, e.g. with a single or two separate solutions containing gene-silencing constructs in a viral vector and corresponding helper virus. The solution(s) may further contain additional compounds to improve inoculation and infection of the plants, such as, but not limited to abrasives, adherents, tensio-active products and the like. Plants may be infected during different developmental stages, in order to maximize the gene-silencing phenotype under investigation. In addition, different parts of plants may be inoculated to optimize observation of the gene-silencing phenotype. Further, when in-vitro RNA transcripts of viral RNA vectors are used, the concentration of the vector RNA used as inoculum-solution may be adapted to at least 10 μg vector RNA per milliliter (10 μg/ml), more preferred at least 50 μg/ml, or even at least 100 μg/ml with buffer. Alternatively, plant tissue of co-infected plants may be ground, and the tissue extract used as inoculum. It has been noticed by the inventors, that increasing the RNA concentration of the inoculum to at least 50 μg/ml or using tissue extract, are both preferred methods of inoculation.

In one embodiment of the invention, a method is provided to introduce inhibitory RNA, using the viral RNA vectors according to the invention, into a plant cell, particularly into the cytoplasm of a plant cell to identify the function of known nucleotide sequences or to validate the hypothetical function of known nucleotide sequences, by inducing silencing of similar sequences in planta.

Hypothetical functions of nucleotide sequences are frequently inferred based on similarity with sequences of known function, or based on the presence of particular sequence motifs, as may be found using computer-assisted analysis using commercially available software packages, such as the Wisconsin Package (Genetics Computer Group, 575 Science Drive, Madison, 53711 Wis., USA). Following such analysis evidence has to be sought, showing that the hypothetical function determined is indeed the real function in planta. Also, the hypothetical function may often only indicate a molecular mode of action of the nucleotide sequence, such as a particular enzyme activity, and it remains unclear what the role of this mode of action is in determining a particular phenotype or trait of the plant. It is generally understood that the functional inactivation of a nucleotide sequence in planta, and the effect this inactivation has on the phenotype of the plant, is a method by which the function of a nucleotide sequence can be determined or validated. To this end, it is preferred that the inactivation of the nucleotide sequence leads to a strong phenotypic change, compared to the wild type plants.

This invention provides methods and means for determining or validating the function, or hypothetical function, of a nucleotide sequence or fragment. In principle, any nucleotide fragment of at least 19, 20 or 21 nucleotides, more preferably at least 27 nucleotides, such as, but not limited to, fragments of about 50, about 100, about 200 nucleotides or more in length can be used in this method. It is not even a requirement to know the sequence of the nucleotide fragment, as the method can be applied without having determined the nucleotide sequence. For example, random clones could be picked from a library and used in the methods of the invention.

The method and vectors of this invention can also be used as a high-throughput gene-function discovery tool, as has been described for the Potato Virus X-based gene-silencing system by Baulcombe (1999), Lu et al. (2000), and Malcuit et al. (2000). A cDNA library can be made and cloned into the vectors of the invention. Subsequently, a large number of plants are co-inoculated with these vectors and helper virus and plants are screened for changes in their phenotype (for example macroscopic, microscopic, biochemical or molecular changes). In this way a relationship between an observed phenotype and a cDNA can be made.

Alternatively, the vectors and methods of the invention can be used in combination with RNA or protein profiling methods for large scale gene discovery or gene expression studies (Bouchez and Höfte, 1998; Ramsay, 1998; Marshall and Hodges, 1998). For example, in order to compare the expression pattern of a large number of genes in silenced versus non-silenced tissue, total mRNA may be isolated from silenced and non-silenced tissue, reverse transcribed into cDNA and used as hybridisation probes for high density DNA- or oligonucleotide-chips or arrays. Similarly protein profiles of silenced and non-silenced tissue may be compared, for example using 2-D gels (Bouchez and Höfte, 1998).

Apart from validating the function of nucleotide sequences, the method of the invention may also be applied in agriculture. It is envisioned that the invention may be used to silence genes which are essential for the normal development of male or female reproductive organs of plants, rendering the treated plants male or female sterile. Viral RNA vectors comprising a gene-silencing construct with sequence identity to (a) gene(s) essential for normal development of the reproductive tissue and corresponding helper virus particles could thus be applied to plants to induce male or female sterility. It can also be envisioned to transform a plant with a vector comprising an inducible or tissue specific promoter active in a plant, operably linked to the nucleotide sequence normally encoding the N-terminal amino acids of the satellite virus coat protein, a short stretch of at least 10 contiguous nucleotides of nucleotides 1365 to 1394 of SEQ ID No 3, and a gene-silencing construct comprising sequence identity (as described elsewhere herein) to (a) gene(s) essential for the normal development of plant tissue (such as, for example, male or female reproductive tissue). Application of the corresponding helper virus at the time of expression or induction of the inducible or tissue specific promoter would lead to absence or abnormal development of the plant tissue. In analogous ways, a viral RNA vector encoding a gene-silencing construct towards genes essential for the growth or normal development of the whole plant may be used to kill whole plants, i.e. as a herbicidal compound.

In another embodiment of the invention methods for obtaining an improved or an enhanced gene-silencing phenotype using the viral RNA vectors according to the invention are provided.

A "gene silencing phenotype" refers to the phenotype of a plant, into which an inhibitory RNA for one or more target genes has been introduced, and where the inhibitory RNA has caused a quantitative or qualitative change in the phenotype compared to the phenotype of plants into which said inhibitory RNA has not been introduced.

Plants may develop a gene-silencing phenotype after co-inoculating tissue with a viral RNA vector derived from a satellite virus comprising a gene-silencing construct and a corresponding helper virus. The gene-silencing phenotype is not observed in plants which are not co-inoculated or in plants which are mock-inoculated with a viral RNA vector without gene-silencing construct and corresponding helper virus. Depending on the function of the endogenous gene(s) of which the expression is modulated, reduced, or eliminated, the gene-silencing phenotype may be morphological, such as chlorosis, necrosis, photobleaching, tissue distortion, or it may be developmental, such as a change in the time of flowering, it may be lethal to, or have severe effects on the normal development of the plant tissue if essential genes are targeted, or it may be molecular, such as changes in concentrations of molecules or metabolites in the tissue. The methods to assay and/or quantify the gene-silencing phenotype may be diverse and may have to be adapted according to each gene silencing phenotype. For a phenotype which manifests in a macroscopically visible phenotype, visual assessment may be made. If the phenotype does not manifest itself in a way that is macroscopically visible alternative methods of assessment may need to be employed. Such methods may comprise analysis of molecule or metabolite presence and/or concentrations, microscopic assays or enzyme assays. This is not to mean that in the case that the phenotype manifests itself in a macroscopically visible phenotype, alternative assays for assessment may not be used, such as but not limited to detection of presence and concentration of mRNA of the target gene(s) in the plant tissue. To assess the enhanced or improved gene silencing phenotype described herein the same assays as described above may be employed.

One embodiment of the invention is to provide a method for obtaining an enhanced gene-silencing phenotype, wherein the method comprises the following steps: providing a viral RNA vector derived from a satellite RNA virus, co-infecting a plant with said vector and a corresponding helper virus or helper virus RNA, waiting for a time-period sufficiently long for the viral vector to establish itself in the plant tissue, removing the apical meristem of the plant, and identifying amongst newly developed tissue, tissue with an altered phenotype.

"Enhanced gene-silencing phenotype" refers to a gene silencing phenotype of secondary tissue of a plant, which is increased in strength and/or uniformity compared to the gene-silencing phenotype of the initially inoculated plant tissue (hereinafter referred to as "primary tissue") of said plant. Preferably the secondary tissue shows a gene-silencing phenotype which is at least 50% stronger and/or at least 50% more uniform than the gene-silencing phenotype of the primary tissue. "Secondary tissue" is used to mean the tissue developing after removal of the apical meristem of the main shoot of a plant. This may comprise newly developed axillary or lateral shoots.

"Strength" is used to mean the degree to which the gene-silencing phenotype is manifested in a tissue of a plant. For a gene-silencing phenotype which manifests itself macroscopically the strength may be the size of the surface area of the tissue which visibly shows the gene-silencing phenotype. An increase in strength would thus refer to an increase in surface area showing the silencing phenotype, compared to the surface area of the primary tissue showing the silencing phenotype. For a gene-silencing phenotype which manifests itself at a biochemical or molecular level, the strength may be the concentration or the presence/absence of a particular molecule or metabolite in the affected tissue. An increase in strength would thus, for example, refer to a reduction of the concentration of a molecule or metabolite in the secondary tissue compared to the concentration in the primary tissue.

"Uniformity" is used to mean the degree of variation of the gene-silencing phenotype between the tissues of a plant, in which the gene-silencing phenotype is manifested. An increase in uniformity refers to a reduction in variation of the gene-silencing phenotype between the tissues of a plant, in which the gene-silencing phenotype is manifested. For example, if the gene-silencing phenotype manifests itself macroscopically as bleaching in leaves 3-7, and each of leaf 3-7 has one large bleached spot, then there is no variation of the gene-silencing phenotype between the leaves (the gene-silencing phenotype is entirely uniform).

With a "time-period sufficiently long for the viral RNA vector to establish itself" it is meant that the co-inoculated plant has to be maintained or kept at normal growth conditions for a time-period which is long enough to allow the viral RNA vector to establish itself in the plant tissue. This period may vary from, for example, 8 to 14 days, particularly from 10 to 12 days, depending on the environmental conditions. The time-period is at least sufficiently long when initial gene-silencing symptoms can be seen.

The "apical meristem" refers to the area of rapidly dividing cells at the tip of the main stem of the plant. It may comprise only a single dividing cell (e.g. in ferns) or it may comprise many cells. It can be removed by physically removing the tip of the plant, either by breaking it off, cutting it off or other physical means. The amount of tissue removed may vary between essentially almost the complete main stem, or removal of only the tissue comprising the apical meristem.

Infection of plant tissue may be carried out using methods as described above.

The viral RNA vector derived from a satellite virus may comprise any of the vectors of the invention described herein above. The viral vector may comprise a nucleotide sequence encoding the N-terminal amino acids of the coat protein. It may further comprise a sequence comprising at least 10 contiguous nucleotides of nucleotides 1365 to 1394 of SEQ ID No 3.

It is another embodiment of the invention to provide a method for obtaining an improved gene-silencing phenotype, the method comprises the following steps:

Providing a T-DNA vector comprising a DNA sequence, which when transcribed yields a viral RNA vector, introducing the T-DNA vector into an *Agrobacterium* strain, inoculating plant tissue with corresponding helper virus particles or RNA and infiltrating said plant tissue with the *Agrobacterium* strain. The T-DNA vector of the invention comprises between right and left border sequences the following operationally linked elements: a promoter active in plant cells, a DNA sequence, which when transcribed yields a viral RNA vector, and a 3' non-translated DNA sequence, which functions in plant cells to cause the termination of transcription and the addition of polyadenylated ribonucleotides to the 3' end of the transcribed mRNA (hereinafter referred to as "3' non-translated sequence"). The DNA sequence, which when transcribed yields a viral RNA vector may be a cDNA copy of the viral RNA vectors of the invention described elsewhere herein. The viral RNA vector comprises a nucleotide sequence encoding the N-terminal amino acids of a satellite virus coat protein and a gene-silencing construct. In one embodiment the T-DNA vector further comprises at least 10 contiguous nucleotides of nucleotides 1365 to 1394 of SEQ ID No 3 between the nucleotide sequence encoding the N-terminal amino acids of the satellite virus coat protein and the gene-silencing construct.

"Improved gene-silencing phenotype" is used to mean a gene-silencing phenotype of primary tissue of a plant, which is increased in strength and/or uniformity compared to the gene-silencing phenotype obtained when known methods for introducing inhibitory RNA into a plant are used. Preferably the primary tissue in which the gene-silencing phenotype is manifested shows a gene-silencing phenotype which is at least 20% stronger and/or at least 20% more uniform than the gene-silencing phenotype obtained when known methods are used.

The construction of T-DNA vectors for *Agrobacterium* mediated plant transformation is well known in the art. The T-DNA vector may be either a binary vector as described by EP0120516 and EP0120515 or a co-integrate vector which can integrate into the Agrobactrium Ti-plasmid by homologous recombination, as described in EP0116718.

Border sequences useful for the present invention are those of SEQ ID No 16 and 17 or described by Gielen et al. (1984). The promoter may be any promoter active in plant cells. The promoter will preferably be a constitutive promoter, such as the Cauliflower Mosaic Virus 35S promoter provided in SEQ ID No 6 or described in U.S. Pat. Nos. 5,352,605 and 5,530,196; enhanced 35S promoter as described in U.S. Pat. No. 5,164,316; the Cassava Vein Mosaic Virus promoter, as described in WO97/48819; the maize ubiquitin promoter, as described in EP342926; the *Arabidopsis* actin 2 promoter as described in An et al. (1996); or the rice actin promoter as described in U.S. Pat. No. 5,641,876. Alternatively a promoter can be utilized which is specific for one or more tissues or organs (e.g. leaves and/or roots) of a plant. For example the light inducible promoter of the gene encoding the small subunit of ribulose 1,5-bisphosphate as described in U.S. Pat. No. 5,034,322 is preferentially active in leaves, while WO00/29566 describes a promoter preferentially active in roots.

Alternatively, an inducible promoter may be used. Such a promoter may be induced after application of a chemical, for example a dexamethasone inducible promoter as described in by Aoyama and Chua (1997) or by a change in temperature, for example a heat shock promoter as described in U.S. Pat. No. 5,447,858 or in Severin and Schoeffl (1990), or a promoter induced by other external stimuli.

3' non-translated sequences are well known in the art and a suitable 3' nontranslated sequence may be obtained from a nopaline synthase gene, such as that of SEQ ID No 15 or from an octopine synthase gene (Gielen et al. 1984) or from the T-DNA gene7 (Velten et al. 1985; Dhaese et al. 1983).

Introduction of the T-DNA vector into *Agrobacterium* can be carried out using known methods, such as for example triparental mating or electroporation.

Tissue infiltration with *Agrobacterium* can be carried out using methods known in the art, such as for example the method described by English et al. (1997). *Agrobacterium* comprising the vector may be suspended in a suitable infiltration medium and delivered to the lamina tissue of leaves by gentle pressure infiltration through the stomata of the lower epidermis, by using a 1 ml needle-less syringe. Alternatively the lower epidermis of the leaf may be slightly wounded, for example by making a few cuts with a razor blade, and the infiltration medium comprising the *Agrobacterium* may be applied to the wounded area with a needle-less syringe. The infiltration method may also involve application of a vacuum following application of the bacteria to the tissue. *Agrobacterium* infiltration may be done before or, preferentially after infection of the tissue with the corresponding helper virus, as long as inoculation and infection are carried out on the same tissue.

The methods of the invention can be applied to essentially all plants for which satellite viral vector and/or corresponding helper viruses are available. The methods of the invention are thought to be particularly suited for *Nicotiana* spp, particularly *N. tabacum, N. sylvestris, N. benthamiana*, and other *Solanacea*, rice (*Oryza sativa*) corn (*Zea mays*), *Brassica* spp., cotton (*Gossypum hirsutum*), wheat, *Arabidopsis* spp., *Petunia* spp.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

The term "gene" means any DNA or RNA fragment comprising a region (the "transcribed region") which is transcribed into an RNA molecule (e.g., an mRNA) in a cell, operably linked to suitable regulatory regions, e.g., a plant-expressible promoter. A gene may thus comprise several operably linked fragments such as a promoter, a 5' leader sequence, a coding region, and a 3' nontranslated sequence, comprising a polyadenylation site. A plant gene endogenous to a particular plant species or virus (endogenous plant or virus gene) is a gene which is naturally found in that plant species or virus, or which can be introduced in that plant species by breeding techniques such as conventional breeding techniques. A chimeric gene is any gene which is not normally found in a plant species or, alternatively, any gene in which the promoter is not associated in nature with part or all of the transcribed DNA region or with at least one other regulatory region of the gene.

The term "expression of a gene" refers to the process wherein a DNA or RNA region which is operably linked to appropriate regulatory regions, particularly to a promoter, is transcribed into an RNA which is biologically active i.e., which is either capable of interaction with another nucleic acid or which is capable of being translated into a biologically active polypeptide or protein. A gene is said to encode an RNA when the end product of the expression of the gene is biologically active RNA, such as e.g. an antisense RNA, a ribozyme or a replicative intermediate. A gene is said to encode a protein when the end product of the expression of the gene is a biologically active protein or polypeptide. In addition to the above defined elements, a gene may further comprise elements for cap-independent translation such as an internal ribosome entry sequence or the first and second translation enhancing elements as defined in WO 97/49814.

For the purpose of this invention the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. The alignment of two sequences is performed using the Needleman and Wunsch algorithm (1970) using a gap creation penalty=50 (nucleotides)/8 (amino acids), a gap extension penalty=3 (nucleotides)/2 (amino acids), and a scoring matrix "nwsgapdna" (nucleotides) or "Blosum62" (amino acids). Alternatively, the alignment of the two sequences is performed using the Wilbur and Lipmann algorithm (Wilbur and Lipmann, 1983) using a window-size of 20 nucleotides or amino acids, a word length of 2 amino acids, and a gap penalty of 4.

Sequence alignments and scores for percent sequence identity between two sequences may be determined using computer programs, such as provided by the Wisconsin Package, Version 10.2, Genetics Computer Group (GCG), 575 Science Drive, Madison, Wis. 53711, USA or Intelligenetics™ Suite (Intelligenetics Inc., CA). For example the progams GAP or BestFit may be used to align two sequences. Alternatively, percent similarity or identity scores are also obtained when searching against databases, such as nucleotide databases FASTA, TFASTA, TFASTX (using algorithms similar to BestFit), BLASTN, TBLASTN, TBLASTX or protein databases FASTA, FASTX, BLASTP, BLASTX.

BestFit makes an optimal alignment of the best segment of similarity between two sequences. Optimal alignments are found by inserting gaps to maximize the number of matches using the local alignment algorithm of Smith and Waterman (1981).

GAP uses the Needleman and Wunsch global alignment algorithm to align two sequences over their entire length, maximizing the number of matches and minimizes the number of gaps. Generally, the default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992).

Sequences are indicated as "essentially similar" when they have a sequence identity of at least about 75%, particularly at least about 80%, more particularly at least 85%, quite particularly at least 90%, especially about 95%, more especially about 100%. It is clear that when RNA sequences are said to be essentially similar or have a certain degree of sequence identity with DNA sequences, thymine (T) in the DNA sequence is considered equal to uracil (U) in the RNA sequence.

The following non-limiting Examples describe the construction of viral RNA vectors derived from satellite viruses, and uses thereof. Unless stated otherwise in the Examples, all recombinant DNA techniques are carried out according to standard protocols as described in Sambrook et al. (1989), in Sambrook and Russell (2001) *Molecular Cloning: A Laboratory Manual*, Third Edition, Cold Spring Harbor Laboratory Press, NY, in Volumes 1 and 2 of Ausubel et al. (1994) Current Protocols in *Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) *PCR Primer: A Laboratory Manual*, Cold Spring Harbor Laboratory Press, and in McPherson et al. (2000) *PCR—Basics: From Background to Bench*, First Edition, Springer Verlag, Germany.

Throughout the description and Examples, reference is made to the following sequences:

SEQ ID No 1: nucleotide sequence of the genome of STMV, comprised in vector pSTMV-10, showing 5 nucleotide differences to SEQ ID No 2. Nucleotides 162 to 641 encode the STMV coat protein. Nucleotides 326 to 331 are recognized by restriction enzyme AgeI.

SEQ ID No 2: nucleotide sequence of the genome of STMV (Genbank Accession No. M25782).

SEQ ID No 3: nucleotide sequence of the tomato phytoene desaturase (pds) encoding cDNA (Genbank Accession No. X59948)

SEQ ID No 4: nucleotide sequence fragment of the tobacco ribulose-biphosphate-carboxylase/oxygenase small subunit (rbcS) encoding cDNA SEQ ID No 5: nucleotide sequence fragment of the tobacco transketolase (tk) encoding cDNA SEQ ID No 6: nucleotide sequence of the Cauliflower Mosaic Virus 35S promoter SEQ ID No 7: nucleotide sequence of the genome of TMV-U2

SEQ ID No 8: nucleotide sequence of the T7 RNA polymerase promoter

SEQ ID No 9: nucleotide sequence of the SP6 RNA polymerase promoter

SEQ ID No 10: 25 bp polylinker nucleotide sequence

SEQ ID No 11: nucleotide sequence fragment of the tobacco acetolactate synthase (als) encoding cDNA SEQ ID No 12: nucleotide sequence fragment of the tobacco repressor of early flowering (cet-2) encoding cDNA SEQ ID No 13: nucleotide sequence fragment of the tobacco cellulose synthase (cesA-1 a) encoding cDNA SEQ ID No 14: nucleotide sequence fragment of the egfp encoding gene (enhanced green fluorescent protein) of *Aequorea victoria*

SEQ ID No 15: nucleotide sequence of the 3' nontranslated sequence of the nopaline synthase gene SEQ ID No 16: nucleotide sequence of the *Agrobacterium tumefaciens* TL-DNA right border sequence SEQ ID No 17: nucleotide sequence of the *Agrobacterium tumefaciens* TL-DNA left border sequence SEQ ID No 18: nucleotide sequence fragment of the tobacco cellulose synthase (cesA-2) encoding cDNA

EXAMPLES

Example 1

Construction of Viral RNA Vectors

In this example the construction of viral RNA vectors targeted to silence endogenous tobacco genes, such as phytoene desaturase (pds), Ribulose-biphosphate-carboxylase/oxygenase (rbcS), transketolase (tk), cellulose synthase (cesA-1a and cesA-2), or a repressor of early flowering (cet-2) is described. Further described are 'basic vectors' into which gene-silencing constructs can easily be inserted. Also the construction of a viral RNA vector comprising two gene-silencing constructs (pds and egfp) is described.

(a) Vector pSTMV-10

To obtain an infectious satellite tobacco mosaic virus clone, a full-length RT-PCR fragment obtained on total RNA of leaves of tobacco plants infected with TMV/STMV (ATCC No. PV-586; tobacco mild green mosaic tobamovirus and satellite) was cloned into pGEM3Z (Promega). The amplified STMV cDNA was sequenced (SEQ ID No 1), revealing 5 single nucleotide differences compared with Genbank Accession No M25782 (SEQ ID No 2; position numbering is based on SEQ ID No 2):

- at position 4-6: in SEQ ID No 1 four A residues are present, instead of three in SEQ ID No 2
- at position 17-20: in SEQ ID No 1 three A residues are present instead of four A residues in SEQ ID No 2
- at position 493: in SEQ ID No 1 an A is present instead of a G in SEQ ID No 2
- at position 596: in SEQ ID No 1 a T is present instead of a C in SEQ ID No 2
- at position 856: SEQ ID No 1 has an additional G SEQ ID No 1 is therefore 1059 nucleotides long, compared to 1058 of SEQ ID No 2.

A vector pSTMV-10 comprising the following operationally linked elements was constructed using conventional molecular techniques:

- a nucleotide sequence comprising SEQ ID No 8 (T7 RNA polymerase promoter)
- a nucleotide sequence comprising SEQ ID No 1 (STMV)
- a nucleotide sequence comprising the reverse compliment of nucleotides 1 to 22 of SEQ ID No 9 (SP6 RNA polymerase promoter)

Using this vector, RNA transcripts, which are infective when inoculated together with helper TMV virus particles or helper virus RNA, were made in vitro.

(b) Vector pVE311, Comprising a Gene-Silencing Construct Targeting Phytoene Desaturase A vector pVE311 was constructed, using standard molecular techniques, by inserting a 195 bp nucleotide fragment of the tomato pds gene (in sense orientation) into the AgeI restriction site of vector pSTMV-10. The pds sequence is thus inserted into the nucleotide sequence encoding the STMV coat protein.

Vector pVE311 comprises the following operationally linked elements:

- a nucleotide sequence comprising SEQ ID No 8 (T7 RNA polymerase promoter)
- a nucleotide sequence comprising nucleotides 1 to 328 of SEQ ID No 1
- a 195 bp fragment of the tomato pythoene desaturase (pds) cDNA comprising nucleotide 1365 to 1559 of SEQ ID No 3
- a nucleotide sequence comprising nucleotides 328 to 1059 of SEQ ID No 1
- a nucleotide sequence comprising the reverse compliment of nucleotides 1 to 22 of SEQ ID No 9 (SP6 RNA polymerase promoter)

(c) Vector pVE344 and pVE330, Comprising a Gene-Silencing Construct Targeting the Small Subunit of Ribulose-Biphosphate-Carboxylase/Oxygenase (rbcS)

A vector pVE344 was constructed, using standard molecular techniques, by replacing most of the pds sequence of vector pVE311 (apart from 21 nucleotides at the 5'end and 22 nucleotides at the 3'end of the pds sequence) with a 151 bp nucleotide fragment of the tobacco rbcS gene (in sense orientation).

Vector pVE344 was constructed using standard molecular techniques, comprising the following operationally linked elements:

- a nucleotide sequence comprising SEQ ID No 8 (T7 RNA polymerase promoter)
- a nucleotide sequence comprising nucleotides 1 to 328 of SEQ ID No 1
- a 21 bp fragment of the tomato phytoene desaturase (pds) cDNA comprising nucleotides 1365 to 1385 of SEQ ID No 3
- a 151 bp fragment of the tobacco rbcS cDNA comprising nucleotides 1 to 151 of SEQ ID No 4 (tobacco rbcS)
- a 22 bp fragment of the tomato phytoene desaturase (pds) cDNA comprising nucleotides 1538 to 1559 of SEQ ID No 3
- a nucleotide sequence comprising nucleotides 328 to 1059 of SEQ ID No 1
- a nucleotide sequence comprising the reverse compliment of nucleotides 1 to 22 of SEQ ID No 9 (SP6 RNA polymerase promoter)

A vector pVE330 was constructed, using standard molecular techniques, by inserting a 151 bp nucleotide fragment of the tobacco rbcS gene (in sense orientation) into the AgeI restriction site of vector pSTMV-10. The rbcS sequence is thus inserted into the nucleotide sequence encoding the STMV coat protein.

Vector pVE330 comprises the following operationally linked elements:

- a nucleotide sequence comprising SEQ ID No 8 (T7 RNA polymerase promoter)
- a nucleotide sequence comprising nucleotides 1 to 330 of SEQ ID No 1
- a 151 bp fragment of the tobacco Ribulose-biphosphate-carboxylase/oxygenase (rbcS) cDNA comprising nucleotide 1 to 151 of SEQ ID No 4
- a nucleotide sequence comprising nucleotides 327 to 1059 of SEQ ID No 1
- a nucleotide sequence comprising the reverse compliment of nucleotides 1 to 22 of SEQ ID No 9 (SP6 RNA polymerase promoter)

(d) Construction of Two 'Basic Vectors', pVE349 and pVE350, Comprising a Polylinker Sequence to Enable Easy Insertion of Gene-Silencing Sequences Downstream of the Short Contiguous Stretch of pds Nucleotides Two 'basic vectors', termed pVE349 and pVE350, were made which are suitable for easy and rapid insertion of gene-silencing sequences. After insertion of gene-silencing sequences the vectors can be used effectively to silence target transgenes or endogenous genes in planta. Vectors derived from these 'basic vectors' will herein carry the superscript bv349 or bv350.

The basic vector pVE349 was constructed, using standard molecular techniques, by replacing most of the pds sequence of vector pVE311 (apart from the 27 nucleotides at the 5' end and 22 nucleotides at the 3' end of the pds sequence) with the polylinker sequence of SEQ ID No 10.

Vector pVE349 was constructed using standard molecular techniques, comprising the following operationally linked elements:

- a nucleotide sequence comprising SEQ ID No 8 (T7 RNA polymerase promoter)
- a nucleotide sequence comprising nucleotides 1 to 328 of SEQ ID No 1
- a 27 bp fragment of the tomato phytoene desaturase (pds) cDNA comprising nucleotides 1365 to 1391 of SEQ ID No 3
- a 25 bp polylinker sequence comprising nucleotides 1 to 25 of SEQ ID No 10
- a 22 bp fragment of the tomato phytoene desaturase (pds) cDNA comprising nucleotides 1538 to 1559 of SEQ ID No 3
- a nucleotide sequence comprising nucleotides 328 to 1059 of SEQ ID No 1
- a nucleotide sequence comprising the reverse compliment of nucleotides 1 to 22 of SEQ ID No 9 (SP6 RNA polymerase promoter)

A vector pVE350 was constructed, using standard molecular techniques, by replacing most of the pds sequence of vector pVE311 (apart from the 27 nucleotides at the 5' end of the pds sequence) and the nucleotide sequence encoding the central amino acids of the STMV coat protein (nucleotides 329 to 600 of SEQ ID No 1) with a polylinker sequence.

Vector pVE350 was constructed using standard molecular techniques, comprising the following operationally linked elements:

- a nucleotide sequence comprising SEQ ID No 8 (T7 RNA polymerase promoter)
- a nucleotide sequence comprising nucleotides 1 to 328 of SEQ ID No 1
- a 27 bp of the tomato phytoene desaturase (pds) cDNA comprising nucleotides 1365 to 1391 of SEQ ID No 3 a 25 bp polylinker sequence comprising nucleotides 1 to 25 of SEQ ID No 10
- a nucleotide sequence comprising nucleotides 603 to 1059 of SEQ ID No 1
- a nucleotide sequence comprising the reverse compliment of nucleotides 1 to 22 of SEQ ID No 9 (SP6 RNA polymerase promoter)

(e) Vectors pVE351$^{bv349}$ and pVE352$^{bv350}$, Comprising a Gene-Silencing Construct Targeting Transketolase (tk)

A vector pVE351$^{bv349}$ was constructed, using standard molecular techniques, by inserting a 200 bp nucleotide fragment of the tobacco tk gene (in antisense orientation) into the polylinker sequence of the 'basic vector' pVE349.

Vector pVE351$^{bv349}$ was constructed using standard molecular techniques, comprising the following operationally linked elements:

- a nucleotide sequence comprising SEQ ID No 8 (T7 RNA polymerase promoter)
- a nucleotide sequence comprising nucleotides 1 to 328 of SEQ ID No 1
- a 27 bp fragment of the tomato phytoene desaturase (pds) cDNA comprising nucleotides 1365 to 1391 of SEQ ID No 3
- a 200 bp fragment of the tobacco transketolase cDNA comprising the reverse complement sequence (antisense) of nucleotides 1 to 200 of SEQ ID No 5 (tk)
- a 22 bp fragment of the tomato phytoene desaturase (pds) cDNA comprising nucleotides 1538 to 1559 of SEQ ID No 3
- a nucleotide sequence comprising nucleotides 328 to 1059 of SEQ ID No 1
- a nucleotide sequence comprising the reverse compliment of nucleotides 1 to 22 of SEQ ID No 9 (SP6 RNA polymerase promoter)

A vector pVE352$^{bv350}$ was constructed, using standard molecular techniques, by inserting a 200 bp nucleotide fragment of the tobacco tk gene (in antisense orientation) into the polylinker sequence of the 'basic vector' pVE350.

Vector pVE352$^{bv350}$ was constructed using standard molecular techniques, comprising the following operationally linked elements:

- a nucleotide sequence comprising SEQ ID No 8 (T7 RNA polymerase promoter)
- a nucleotide sequence comprising nucleotides 1 to 328 of SEQ ID No 1
- a 27 bp of the tomato phytoene desaturase (pds) cDNA comprising nucleotides 1365 to 1391 of SEQ ID No 3
- a 200 bp fragment of the tobacco transketolase cDNA comprising the reverse complement sequence (antisense) of nucleotides 1 to 200 of SEQ ID No 5 (tk)
- a nucleotide sequence comprising nucleotides 601 to 1059 of SEQ ID No 1
- a nucleotide sequence comprising the reverse compliment of nucleotides 1 to 22 of SEQ ID No 9 (SP6 RNA polymerase promoter)

(f) Vectors pVE375$^{bv349}$ and pVE376$^{bv350}$, Comprising a Gene-Silencing Construct Targeting Acetolactate Synthase (als)

A vector pVE375$^{bv349}$ was constructed, using standard molecular techniques, by inserting a 207 bp nucleotide fragment of the tobacco als gene (in sense orientation) into the polylinker sequence of the 'basic vector' pVE349.

Vector pVE375$^{bv349}$ was constructed using standard molecular techniques, comprising the following operationally linked elements:

- a nucleotide sequence comprising SEQ ID No 8 (T7 RNA polymerase promoter)
- a nucleotide sequence comprising nucleotides 1 to 328 of SEQ ID No 1
- a 27 bp fragment of the tomato phytoene desaturase (pds) cDNA comprising nucleotides 1365 to 1391 of SEQ ID No 3
- a 207 bp fragment of the tobacco acetolactate synthase (als) cDNA comprising nucleotides 1 to 207 of SEQ ID No 11
- a 22 bp fragment of the tomato phytoene desaturase (pds) cDNA comprising nucleotides 1538 to 1559 of SEQ ID No 3
- a nucleotide sequence comprising nucleotides 328 to 1059 of SEQ ID No 1
- a nucleotide sequence comprising the reverse compliment of nucleotides 1 to 22 of SEQ ID No 9 (SP6 RNA polymerase promoter)

A vector pVE376$^{bv350}$ was constructed, using standard molecular techniques, by inserting a 207 bp nucleotide fragment of the tobacco als gene (in sense orientation) into the polylinker sequence of the 'basic vector' pVE350.

Vector pVE376$^{bv350}$ was constructed using standard molecular techniques, comprising the following operationally linked elements:

- a nucleotide sequence comprising SEQ ID No 8 (T7 RNA polymerase promoter)
- a nucleotide sequence comprising nucleotides 1 to 328 of SEQ ID No 1
- a 27 bp of the tomato phytoene desaturase (pds) cDNA comprising nucleotides 1365 to 1391 of SEQ ID No 3
- a 207 bp fragment of the tobacco acetolactate synthase (als) cDNA comprising nucleotides 1 to 207 of SEQ ID No 11
- a nucleotide sequence comprising nucleotides 601 to 1059 of SEQ ID No 1
- a nucleotide sequence comprising the reverse compliment of nucleotides 1 to 22 of SEQ ID No 9 (SP6 RNA polymerase promoter)

(g) Vectors pVE353$^{bv349}$ and pVE354$^{bv350}$, Comprising a Gene-Silencing Construct Targeting the cet-2 "Repressor of Early Flowering"

A vector pVE353$^{bv349}$ was constructed, using standard molecular techniques, by inserting a 224 bp nucleotide fragment of the tobacco cet-2 gene (in sense orientation) into the polylinker sequence of the 'basic vector' pVE349.

Vector pVE353$^{bv349}$ was constructed using standard molecular techniques, comprising the following operationally linked elements:

- a nucleotide sequence comprising SEQ ID No 8 (T7 RNA polymerase promoter)
- a nucleotide sequence comprising nucleotides 1 to 328 of SEQ ID No 1
- a 27 bp fragment of the tomato phytoene desaturase (pds) cDNA comprising nucleotides 1365 to 1391 of SEQ ID No 3
- a 224 bp fragment of the tobacco cet-2 cDNA comprising nucleotides 1 to 224 of SEQ ID No 12
- a 22 bp fragment of the tomato phytoene desaturase (pds) cDNA comprising nucleotides 1538 to 1559 of SEQ ID No 3
- a nucleotide sequence comprising nucleotides 328 to 1059 of SEQ ID No 1
- a nucleotide sequence comprising the reverse compliment of nucleotides 1 to 22 of SEQ ID No 9 (SP6 RNA polymerase promoter)

A vector pVE354$^{bv350}$ was constructed, using standard molecular techniques, by inserting a 224 bp nucleotide fragment of the tobacco cet-2 gene (in sense orientation) into the polylinker sequence of the basic vector pVE350.

Vector pVE354$^{bv350}$ was constructed using standard molecular techniques, comprising the following operationally linked elements:

a nucleotide sequence comprising SEQ ID No 8 (T7 RNA polymerase promoter)

a nucleotide sequence comprising nucleotides 1 to 328 of SEQ ID No 1 a 27 bp of the tomato phytoene desaturase (pds) cDNA comprising nucleotides 1365 to 1391 of SEQ ID No 3 a 224 bp fragment of the tobacco cet-2 cDNA comprising nucleotides 1 to 224 of SEQ ID No 12 a nucleotide sequence comprising nucleotides 601 to 1059 of SEQ ID No 1 a nucleotide sequence comprising the reverse compliment of nucleotides 1 to 22 of SEQ ID No 9 (SP6 RNA polymerase promoter)

(h) Vectors pVE369$^{bv349}$, pVE370$^{bv350}$ and pVE377$^{bv349}$, Comprising a Gene-Silencing Construct Targeting Cellulose Synthase (cesA-1a or cesA-2)

A vector pVE369$^{bv349}$ was constructed, using standard molecular techniques, by inserting a 195 bp nucleotide fragment of the tobacco cellulose synthase cesA-1a gene (in sense orientation) into the polylinker sequence of the 'basic vector' pVE349.

Vector pVE360$^{bv349}$ was constructed using standard molecular techniques, comprising the following operationally linked elements:

a nucleotide sequence comprising SEQ ID No 8 (T7 RNA polymerase promoter)

a nucleotide sequence comprising nucleotides 1 to 328 of SEQ ID No 1 a 27 bp fragment of the tomato phytoene desaturase (pds) cDNA comprising nucleotides 1365 to 1391 of SEQ ID No 3 a 195 bp fragment of the tobacco cellulose synthase (ces1A) cDNA comprising nucleotides 1 to 195 of SEQ ID No 13 a 22 bp fragment of the tomato phytoene desaturase (pds) cDNA comprising nucleotides 1538 to 1559 of SEQ ID No 3 a nucleotide sequence comprising nucleotides 328 to 1059 of SEQ ID No 1 a nucleotide sequence comprising the reverse compliment of nucleotides 1 to 22 of SEQ ID No 9 (SP6 RNA polymerase promoter)

A vector pVE370$^{bv350}$ was constructed, using standard molecular techniques, by inserting a 195 bp nucleotide fragment of the tobacco cellulose synthase cesA-1a gene (in sense orientation) into the polylinker sequence of the 'basic vector' pVE350.

Vector pVE370$^{bv349}$ was constructed using standard molecular techniques, comprising the following operationally linked elements:

a nucleotide sequence comprising SEQ ID No 8 (T7 RNA polymerase promoter)

a nucleotide sequence comprising nucleotides 1 to 328 of SEQ ID No 1 a 27 bp of the tomato phytoene desaturase (pds) cDNA comprising nucleotides 1365 to 1391 of SEQ ID No 3 a 195 bp fragment of the tobacco cellulose synthase (ces1A) cDNA comprising nucleotides 1 to 195 of SEQ ID No 13 a nucleotide sequence comprising nucleotides 601 to 1059 of SEQ ID No 1 a nucleotide sequence comprising the reverse compliment of nucleotides 1 to 22 of SEQ ID No 9 (SP6 RNA polymerase promoter)

A vector pVE377$^{bv349}$ was constructed, using standard molecular techniques, by inserting a 260 nucleotide fragment of the tobacco cellulose synthase cesA-2 gene (in sense orientation) into the polylinker sequence of the 'basic vector' pVE349.

Vector pVE377$^{bv349}$ was constructed using standard molecular techniques, comprising the following operationally linked elements:

a nucleotide sequence comprising SEQ ID No 8 (T7 RNA polymerase promoter)

a nucleotide sequence comprising nucleotides 1 to 328 of SEQ ID No 1 a 27 bp fragment of the tomato phytoene desaturase (pds) cDNA comprising nucleotides 1365 to 1391 of SEQ ID No 3 a 260 bp fragment of the tobacco cellulose synthase (cesA-2) cDNA comprising nucleotides 1 to 260 of SEQ ID No 18 a 22 bp fragment of the tomato phytoene desaturase (pds) cDNA comprising nucleotides 1538 to 1559 of SEQ ID No 3 a nucleotide sequence comprising nucleotides 328 to 1059 of SEQ ID No 1 a nucleotide sequence comprising the reverse compliment of nucleotides 1 to 22 of SEQ ID No 9 (SP6 RNA polymerase promoter)

(i) Vectors pVE367 and pVE368, Each Vector Comprising Two Gene-Silencing Constructs (pds and egfp)

A vector pVE367 was constructed, using standard molecular techniques, by inserting a 102 bp nucleotide fragment of the egfp gene (in sense orientation) into the 195 bp pds sequence of vector pVE311. The egfp sequence was inserted downstream of the initial 21 bp of the tomato pds sequence.

Vector pVE367 comprises the following operationally linked elements:

a nucleotide sequence comprising SEQ ID No 8 (T7 RNA polymerase promoter)

a nucleotide sequence comprising nucleotides 1 to 328 of SEQ ID No 1 a 21 bp fragment of the tomato pythoene desaturase (pds) cDNA comprising nucleotide 1365 to 1385 of SEQ ID No 3 a 102 bp fragment of the egfp gene comprising nucleotides 1 to 102 of SEQ ID No 14 a nucleotide sequence comprising nucleotides 1390 to 1559 of SEQ ID No 3 (pds)

a nucleotide sequence comprising nucleotides 328 to 1059 of SEQ ID No 1 a nucleotide sequence comprising the reverse compliment of nucleotides 1 to 22 of SEQ ID No 9 (SP6 RNA polymerase promoter)

Vector pVE368 is equivalent to vector pVE367, with the difference that the 102 bp egfp fragment inserted is the reverse complement sequence (antisense) of SEQ ID No 14.

Example 2

Silencing of Tobacco Genes

To compare multiplication, spread and ability to induce gene-silencing of vectors constructed as per Example 1 in *Nicotiana tabacum* SR1, tobacco plants were grown under long day-light, 25° C. and at 85% relative humidity. The youngest fully developed leaf of 6-8 week old plants was brushed with carborundum and mechanically co-inoculated with leaf extracts comprising TMV helper virus particles and in-vitro transcripts of vectors of Example 1. At least five plants were inoculated per vector. As controls a number of plants were mock-inoculated and a number of plants were co-inoculated with wild type TMV/STMV. Experiments were repeated several times.

Infective in vitro transcripts were generated using T7 RNA polymerase, with the linearized plasmid DNAs of the described vectors as templates. The RNA was recovered by lithium chloride precipitation and the concentration adapted to 50 μg/ml with 0.2M sodium-phosphate buffer (pH 7).

TMV helper virus particles were prepared by grinding TMV-infected tobacco leaves in 0.2M sodium phosphate buffer and applying this leaf extract shortly after the vector RNA.

(a) Phytoene Desaturase (pds)

Six week old tobacco plants were co-inoculated with in-vitro transcripts of pVE311 and TMV helper virus particles. Ten days post inoculation the third leaf above the inoculated leaf started showing the expected gene-silencing phenotype, manifested as "bleaching".

"Bleaching", or photobleaching, as used herein refers to the white phenotype of tissue, which develops when the enzyme phytoene desaturase, which is part of the carotenoid biosynthetic pathway, is rendered non-functional. A bleached phenotype can be obtained following treatment of tissue with the herbicide norflurazon, a non-competitive inhibitor of pds (Kumagai et al. 1995). As a consequence of herbicide treatment, there is a dramatic decrease in carotenoids and chlorophylls, while phytoene accumulates. The reduction of the photoprotective carotenoids may lead to a rapid destruction of chlorophylls by photooxidation (the tissue becomes white).

Bleaching started around the veins and extended progressively into the leaf sectors in the following three days. During the following six days the intensity of bleaching increased until large sectors of the leaf lamina or the whole leaf lamina showed a bleached phenotype. The third-fourth to about sixth-seventh leaf above the inoculated leaf showed strong bleaching, affecting large sectors or even the entire leaf lamina. The bleaching phenotype became progressively reduced from about the eighth-ninth leaf onwards, with bleached sectors becoming smaller and interspersed by more and larger green islands. Gene-silencing symptoms were highly reproducible, affecting repeatedly 90-100% of inoculated plants.

Northern blot analysis showed the presence of RNA of the TMV helper virus and the chimeric satellite virus pVE311 both in the green tissue of the inoculated leaf (5 ng/μg total RNA) and in the bleached tissue of upper leaves (20 pg-500 pg/μg total RNA), proving the systemic spread of both viruses. Northern blot analysis further showed that pds mRNA levels were drastically reduced in the bleached tissue of upper leaves (<0.5 pg/10 μg total RNA), but not in the green tissue of the inoculated leaf (~2 pg/10 μg total RNA). This indicates that the chimeric satellite virus pVE311 was able to replicate and move systemically from the inoculated leaf to upper leaves and was efficient in silencing the endogenous phytoene desaturase in upper leaves.

Typically TMV-U2 infection causes mild symptoms in tobacco, such as distortion of tissue, dark spots, reduced leaf and plant size. Co-inoculation with chimeric satellite virus vectors attenuated the already normally weak TMV-U2 helper virus symptoms to almost undetectable levels.

In some cases bleaching was also observed in stem and flower tissues, such as sepals and carpels. There was a correlation between the leaves with a pronounced bleaching phenotype and bleaching of the stem sectors to which these leaves were attached. Virus induced gene silencing using this system can thus be used to induce gene-silencing in different plant tissues and organs.

This example shows that an RNA vector comprising a 195 bp fragment of the tomato pds cDNA inserted in sense orientation at the AgeI site into the nucleotide sequence encoding the STMV coat protein (i.e. downstream of the nucleotide sequence normally encoding the N-terminal amino acids of the STMV coat protein) can effectively replicate and spread systemically in tobacco and can effectively induce silencing of endogenous tobacco phytoene desaturase genes in different tissues, such as leaves, flowers and stems.

(b) Ribulose-Biphosphate-Carboxylase/Oxygenase Small Subunit (rbcS)

Six week old tobacco plants were co-inoculated with in-vitro transcripts of pVE344 and TMV helper virus particles. Ten days post inoculation the third leaf above the inoculated leaf started showing the expected gene-silencing phenotype, manifested as "chlorosis". "Chlorosis" as used herein refers to as pale-green discoloration of photosynthetically active tissue, following silencing of rbcS, compared to the deep-green color of non-silenced tissue. Further, plants showed stunted growth.

Chlorosis started around the veins and extended progressively into the leaf sectors. Within a few days the intensity of chlorosis increased until large sectors of the leaf lamina or the whole leaf lamina showed a chlorotic phenotype. The third to about sixth-seventh leaf above the inoculated leaf showed strong chlorosis, affecting large sectors or even almost the entire leaf lamina. Gene-silencing symptoms were highly reproducible, affecting repeatedly 100% of inoculated plants. There were no signs of photobleaching in any of the inoculated plants, indicating that the presence of 21 nucleotides of the tomato pds gene, preceding the gene-silencing construct, was not able to cause gene-silencing of the endogenous tobacco pds gene.

Northern blot analysis showed the presence of RNA of the TMV helper virus and the chimeric satellite virus pVE344 in chlorotic tissue (50 pg/μg total RNA), proving the systemic spread of both viruses. In the green tissue of the inoculated leaf virus RNA levels were 5 ng/μg total RNA. Northern blot analysis further showed that rbcS mRNA levels were drastically reduced in the chlorotic tissue (<0.5 pg/μg total RNA). In comparison, ~300 pg/μg total RNA was detected in green, non-inoculated tissue. This indicates that the chimeric satellite virus pVE344 was able to replicate and move systemically from the inoculated leaf to upper leaves and was efficient in silencing the endogenous ribulose-biphosphate-carboxylase/oxygenase in upper leaves.

Analogous experiments conducted with pVE330, which also comprises a 151 bp fragment of tobacco rbcS cDNA inserted in sense orientation into the AgeI site of the nucleotide sequence encoding the STMV coat protein, but which differs from pVE344 in that the two short nucleotide fragments comprising 21 nucleotides (the 5' end) and 22 nucleotides (the 3' end) of the tomato pds cDNA fragment are absent. In contrast to pVE344, pVE330 did not induce gene-silencing symptoms in tobacco plants. Northern blot analysis indicated that pVE330 RNA was not detectable in upper leaf tissue, indicating that the chimeric satellite virus pVE330 was not able to replicate and spread in planta. This indicated, that the presence of nucleotides of the pds gene in pVE344 surprisingly had an effect on the ability to induce gene-silencing in planta. The following Example 2(c) shows that in particular the presence of the short contiguous stretch of pds nucleotides preceding the gene-silencing construct enabled the ability to induce gene-silencing. Based on this finding two 'basic vectors' (pVE349 and pVE350) were constructed, which would enable easy cloning of gene-silencing sequences downstream of the nucleotide sequence encoding the N-terminal amino acids of the STMV coat protein (nucleotides 162 to 328 of SEQ ID No 1) and a short stretch of at least 10 contiguous nucleotides of SEQ ID No 3 (pds). The efficient use of these basic vectors for inducing gene-silencing in planta is demonstrated in Examples 2(c)-2(g).

The present example indicated that endogenous tobacco rbcS, a gene expressed at high levels in photosynthetically active tissue, could be silenced, if the gene-silencing sequence, rbcS, was inserted into the RNA vector between two short stretches of contiguous nucleotides of the nucleotide sequence encoding tomato phytoene desaturase. In contrast, the use of an RNA vector (pVE330), which did not comprise these short stretches of contiguous pds nucleotides, did not induce a gene-silencing phenotype in tobacco and the RNA vector was not able to replicate and spread in tobacco plants.

(c) Transketolase

Six week old tobacco plants were co-inoculated with in-vitro transcripts of pVE351$^{bv349}$ or pVE352$^{bv350}$ and TMV helper virus particles. Ten days post inoculation the third leaf above the inoculation site started showing the expected gene-silencing phenotype around the veins, manifested as "yellow-red discoloration". Yellow-red discoloration as used herein refers to the phenotypic pale, yellow-red discoloration of tissue in which transketolase is silenced, as seen by Henkes et al. (2001) in tobacco transformed with an antisense transketolase construct. In antisense transketolase transformants photosynthesis and phenylpropanoid metabolism are severely affected and the physiological changes are accompanied by an easy to detect tissue discoloration.

Yellow-red discoloration started around the veins and extended progressively into the leaf sectors. Within a few days the intensity of yellow-red discoloration increased, until large sectors of the leaf lamina or the whole leaf lamina showed a yellow-red phenotype. The third to about sixth-seventh leaf above the inoculated leaf showed strong yellow-red discoloration, affecting large sectors or even almost the entire leaf lamina. Gene-silencing symptoms were highly reproducible, affecting repeatedly 50-100% of inoculated plants. There were few, occasional spots of photobleaching on yellow-red leaves, indicating that the presence of 27 nucleotides of the tomato pds gene, preceding the gene-silencing construct, did induce some gene-silencing of the endogenous tobacco pds gene. However, the bleaching did not interfere with the analysis of the transketolase silencing phenotype.

Northern blots indicated the reduction of tk mRNA in yellow-red discolored tissue. Plants grew slower than untreated controls, but survived for many months.

Essentially the same results were obtained when experiments were carried out with RNA transcripts from vectors pVE357$^{bv349}$ or pVE358$^{bv350}$ (results not shown), which are identical to pVE351$^{bv349}$ and pVE352$^{bv350}$ respectively, with the difference that the 200 bp transketolase fragment is present in sense orientation instead of antisense orientation.

This example indicated that endogenous tobacco tk, a gene expressed at moderate levels in tobacco leaves (higher than pds but lower than rbcS), could be silenced, if the gene-silencing sequence, tk, was inserted into the RNA vector following a short stretch of contiguous nucleotides of the nucleotide sequence encoding tomato phytoene desaturase. Further, results indicated that the pds sequence preceding the gene-silencing construct may vary in length, as exemplified herein by comparing vectors comprising either a stretch of 21 or 27 nucleotides of pds (in sense orientation) 5' to the gene-silencing construct.

In addition, both pVE351$^{bv349}$ and pVE352$^{bv350}$ transcripts were able to induce strong gene-silencing, indicating, that the short stretch of contiguous pds nucleotides 3' to the gene-silencing construct (nucleotides 1538-1559 of SEQ ID No 3), as well as part of the nucleotide sequence encoding the coat protein gene (nucleotides 329 to 600 of SEQ ID No 1), can be removed (as exemplified with pVE352$^{bv350}$), without diminishing the ability of the vector to replicate, move systemically and induce gene-silencing. This shows that in particular the presence of the short contiguous stretch of pds nucleotides preceding the gene-silencing construct enabled the ability of the vector to induce gene-silencing.

(d) Acetolactate Synthase (als)

The enzyme acetolactate synthase (als) is one of the key enzymes in the aromatic amino acid synthesis pathway. The gene-silencing of this enzyme was therefore expected to result in disturbances of normal plant development.

Six weeks old tobacco plants were co-inoculated with in-vitro transcript of pVE375$^{bv349}$ or pVE376$^{bv350}$ and TMV helper virus particles. Ten days post inoculation the third leaf above the inoculated leaf started showing the expected gene-silencing phenotype, manifested as "leaf distortion and pigment deregulation". "Leaf distortion and pigment deregulation" as used herein refers to the extreme deformation (crinkling and development of deep kurfs) seen in newly emerging leaves of co-inoculated plants and the light-green/dark-green mosaic pigmentation pattern of the leaves of co-inoculated plants, compared to the absence of these symptoms in control plants. Approximately four weeks later the plants recovered and started to develop normally pigmented and normally shaped leaves.

This example indicated that endogenous tobacco als gene or gene-family could effectively be silenced, if a als sequence was inserted into either of the two 'basic' RNA vectors pVE349 and pVE350 downstream of a short stretch of contiguous nucleotides of nucleotides 1365 to 1394 of SEQ ID No 3.

(e) cet-2 "Repressor of Early Flowering"

The tobacco "repressor of early flowering" is encoded by a family of cet genes, which have homology to well-studied cen-genes in *Antirrhinum majus*. The genes are expressed in apical and axillary meristems of young, not yet flowering plants (Amaya et al. 1999). The gene products act as repressors and delay the commitment to flower. Gene-silencing of these repressors should result in a shift towards earlier flowering compared to non-silenced plants.

Six weeks old tobacco plants were co-inoculated with in-vitro transcripts of pVE353$^{bv349}$ or pVE354$^{bv350}$ and TMV helper virus particles. The expected gene-silencing phenotype would be manifested as "early flowering". "Early flowering" as used herein means that the shift from vegetative phase to reproductive phase (flower induction), which occurs in the meristem tissue, occurs at an earlier time-point in the gene-silenced plants than in non-silenced plants.

Tobacco plants flower under defined growth conditions (20-25° C., 16 hours light, 8 hours darkness) normally 12 weeks post germination. In two separate experiments for each vector five out of ten plants inoculated with pVE353$^{bv349}$ or pVE354$^{bv350}$ flowered already 9 weeks post germination, which is three weeks post inoculation. All mock inoculated and wild-type satellite virus infected plants flowered three weeks later, 12 weeks post germination or six weeks post inoculation. That not all co-inoculated plants displayed the expected silencing phenotype is possibly due to the complexity of the developmental and environmental control of flowering.

This example indicated that genes expressed in meristem tissue, such as the tobacco cet-2 gene or gene family can be silenced effectively using the vectors and methods described herein.

(f) Cellulose Synthase (cesA-1a, cesA-2)

The targeted genes cesA-1a and cesA-2 both encode cellulose synthase enzymes, which are involved in cellulose synthesis and thereby in cell wall assembly. Gene-silencing of these enzymes should result in dramatic disturbances of leaf development and growth, as described by Burton et al. (2000).

Six weeks old tobacco plants were co-inoculated with in-vitro transcripts of pVE369$^{bv349}$ or pVE370$^{bv350}$ for cesA-1a or pVE377$^{bv349}$ for cesA-2 and TMV helper virus particles. In all cases, ten days post co-inoculation the third leaf above the inoculated leaf started showing the expected gene-silencing phenotype, manifested as "leaf distortion and chlorosis". "Leaf distortion and chlorosis" is used herein to mean the deformations, discoloration and changes in surface texture seen in cellulose synthase silenced plants.

In case of cesA-1a chlorosis started around the veins and extended progressively into the leaf sectors within three days. During the following two weeks newly emerging leaves showed heavy deformations and finally developed numerous clumps of expanded cells on the leaf surface. The plants grew significantly slower than virus-infected control plants. After approximately another two weeks the plants showed a recovery phenotype. Newly emerging leaves turned green again and the leaf distortions disappeared.

In case of cesA-2 a similar leaf distortion and chlorosis could be observed but the symptoms were less severe than for cesA-1a. The chlorotic leaves did not develop clumps and showed generally less deformation. However, the growth inhibition was stronger than for cesA-1a silenced plants and the plants stayed in a dwarfism phase for many weeks.

The results indicated that endogenous genes expressed at low levels in most plant tissues could effectively be silenced using the vectors and methods of the invention.

(g) egfp (Transgene) and pds (Endogenous Gene) Double Knockouts Using a Single Vector In order to test whether two gene-silencing constructs incorporated into a single viral RNA vector could effectively induce silencing of a transgene target and an endogenous gene target simultaneously, a 102 bp fragment of the gene encoding enhanced green fluorescent protein (egfp) was inserted into the 195 bp cDNA fragment of the gene encoding tomato phytoene desaturase.

The egfp fragment was inserted either in sense or in antisense orientation into vector pVE311, so that 21 nt of the pds sequence preceded the egfp sequence, resulting in vectors pVE367 and pVE368, respectively (see Example 1).

Six weeks old transgenic tobacco plants carrying a homozygous single copy egfp transgene under the control of the 35S promoter were co-inoculated with in-vitro transcripts of pVE367 or pVE368 and TMV helper virus particles. The two expected gene-silencing phenotypes would be manifested as "bleaching", as described for the pds gene-silencing phenotype (see Example 2a), and as "loss of green fluorescence" for silencing of the egfp transgene.

The transgenic tobacco plants used in this example expressed the single-copy egfp gene at high level due to the 35S promoter. Northern analyses showed high levels of egfp specific mRNA. The green fluorescence was easily detectable with a UV-handlamp in all leaf and stem tissues and was especially strong in young emerging leaves and the stem apex.

Ten days post inoculation all plants inoculated with the chimeric egfp/pds satellite virus double constructs showed independent of the insert orientation (sense in case of pVE367, antisense in case of pVE368) the expected pds bleaching. In the white pds-silenced leaf tissue no green fluorescence could be observed under UV light, indicating that also the egfp transgene had been silenced. No green fluorescence was detectable with the UV-handlamp in any of the white tissue sectors. At this stage the green fluorescence was still detectable in stem tissue and young emerging leaves near the apex.

Within another week the pds gene-silencing phenotype developed systemically as observed before for the single pds knockouts (Example 2a), but was in case of the double insert constructs always accompanied by silencing of the egfp transgene. No interference with the timing or extent of pds silencing was observed.

The results indicate that several gene-silencing constructs can be inserted into a single satellite virus RNA vector, either in tandem or inserted into each other. Thereby the simultaneous silencing of more than one target gene can be achieved. Further, it is possible to silence several endogenous target genes, or several transgenes or a combination of both, using a single viral RNA vector.

Example 3

Enhanced Gene-Silencing Phenotype After Removal of the Apical Meristem

The following method provides a way by which a gene-silencing phenotype can be enhanced, to obtain a stronger and/or more uniform phenotype.

Tobacco plants were co-inoculated with in vitro transcripts of pVE311 and helper virus particle, as described in Example 2a. Ten to twelve days post inoculation plants were selected which showed moderate signs of pds gene-silencing, in that a number of leaves were green-white variegated. From these plants the apical meristem was removed by cutting off the top of the main stem with a razor blade.

Seven days after removal of the apical meristem a number of secondary shoots had emerged from lower axillary meristems of the pds-silenced plants. Surprisingly, the gene-silencing phenotype in all secondary leaves was much stronger (instead of the green-white variegation seen in primary leaves, secondary leaves were almost completely white) and the gene-silencing phenotype of secondary leaves was much more uniform (all secondary leaves were uniformly bleached, compared to variation in the gene-silencing phenotype of primary leaves, where some leaves were highly variegated, and some weakly variegated).

The data indicate that the silencing phenotype can be enhanced by removal of the apical meristem and induction of secondary growth. Such enhancement may be important for determining or validating the function of genes, especially if the silencing did not induce a strong and/or uniform gene-silencing phenotype in the primary tissue of the co-inoculated plant.

Example 4

Improved Gene-Silencing Phenotypes by *Agrobacterium* Infiltration

The following method leads to an improved gene-silencing phenotype when compared to known methods.

A T-DNA vector, pTVE334, was constructed using standard molecular techniques, carrying the following operationally linked elements:

- a nucleotide sequence comprising SEQ ID No 16 (RB)
- a nucleotide sequence comprising SEQ ID No 6 (Cauliflower Mosaic Virus 35S promoter)
- a nucleotide sequence comprising nucleotides 1 to 328 of SEQ ID No 1
- a 195 bp fragment of the tomato phytoene desaturase (pds) cDNA comprising nucleotides 1365 to 1559 of SEQ ID No 3
- a nucleotide sequence comprising nucleotides 328 to 1059 of SEQ ID No 1
- a nucleotide sequence comprising SEQ ID No 15 (3'nopaline synthase)
- a nucleotide sequence comprising SEQ ID No 17 (LB)

The TDNA vector was transformed into *Agrobacterium tumefaciens* strain C58C1Rif (pGV3000). *Agrobacterium* cells were grown overnight at 28° C. in 5 ml Luria Broth containing streptomycin and spectinomycin. Cells were precipitated and resuspended in Murashige and Skoog medium with 2% sucrose, 500 μM MES pH 5.6 and 10 μM acetosyringone to an $O.D._{600}$ of 1 and incubated at room temperature for 3 hours before infiltration. Young tobacco leaves were first inoculated with TMV helper virus particle. *Agrobacterium* infiltration was done on the underside of the same leaf: with a razor blade 4-6 holes were made on the underside of the leaf and the *Agrobacterium* cells were injected with a syringe.

Ten days post inoculation the third leaf above the inoculated leaf showed first signs of bleaching around the major veins. The following newly emerging leaves 4-7 showed a progressively more severe gene-silencing phenotype. Leaves 5-7 were almost uniformly white, apart from very few small green islands. In later developed leaves, the gene-silencing phenotype decreased, e.g. leaf 9 was green and the following leaves were showed a highly variegated pattern of green and white spots. 100% of treated plants showed a very strong gene-silencing phenotype.

The results indicated that this method was able to enhance uniformity and strength of the gene-silencing phenotype, compared to methods known in the art.

Example 5

Additional Examples of Silencing Endogenous Tobacco Genes

In addition to the silencing of pds, rbcS, tk, als, cesA-1a and cesA-2, as described in the Examples above (and in the table below), a range of additional tobacco genes were silenced by inserting cDNA fragments of various sizes (as indicated in the table below) into the polylinker of the basic vector pVE349. Target fragments were inserted either in sense or in antisense orientation. The experimental setup was as described above. The gene-silencing phenotypes observed are summarized in the table below:

| Target | Insert size | Phenotypic leaf changes | | | |
|---|---|---|---|---|---|
| gene | (bp) | location | phenotype | Growth | Flowering |
| chsA | 173 | Inoculated and upper leaves | Chlorotic spots | normal | Variegated petals |
| ppx-1 | 216 | Upper leaves | Chlorotic, necrosis, small holes | stunted | delayed |
| gln1-5 | 203 | Upper leaves | Chlorotic, small, vascular necrosis | stunted | delayed |
| rpII-a | 142 | Upper leaves | White (bleached), deformed, very small | stunted | none |
| cat-1 | 171 | Inoculated and upper leaves | Chlorotic spots, necrosis | normal | normal |
| npk-1 | 161 | Inoculated and upper leaves | Chlorotic spots, necrosis | normal | normal |
| parp | 161 | Inoculated and upper leaves | Chlorotic spots, necrosis | normal | normal |
| pds | 195 | Upper leaves | White (bleached), small | stunted | Delayed, few white sepals and carpels |
| rbcS | 151 | Upper leaves | Chlorotic, small | stunted | normal |
| tk | 200 | Upper leaves | Chlorotic (yellow-red discoloration) | Slightly stunted | normal |
| CesA-1a | 195 | Upper leaves | Chlorotic and leaf distortion (crinkeled, many lumps) | stunted | none |
| CesA-2 | 205 | Upper leaves | Chlorotic and leaf distortion (crinkeled, few lumps) | stunted | none |
| als | 207 | Upper leaves | Leaf distortion and pigment deregulation (chlorotic, crinkeled, dark green spots) | stunted | early |

Target genes, nucleotides of GenBank Accession numbers or of SEQ ID No's:

- chsA (*Nicotiana tabacum* chalcone synthase A cDNA), AF311783, 898-1070 bp
- ppx-1 (*Nicotiana tabacum* protoporphyrin IX oxidase cDNA), Y13465, 1201-1416 bp
- gln 1-5 (glutamine synthetase), X95932, 597-799 bp
- rpll-a (RNA polymerase ll-a), AF153277, 224-365 bp
- cat-1 (*Nicotiana tabacum* catalase 1 cDNA), U93244, 1231-1401 bp
- npk-1 (*Nicotiana* protein kinase 1 cDNA), D26601, 1771-1931 bp
- parp (*A. thaliana* poly ADP-ribose polymerase cDNA), Z48243, 1570-1730 bp
- pds (*L. esculentum* phytoene desaturase cDNA nucleotides 1365 to 1559 of SEQ ID No 3
- rbcS (*Nicotiana* small subunit ribulose-biphosphate carboxylase/oxygenase cDNA), X02353, 1067 to 1217 bp
- tk (transketolase cDNA) nucleotides 1 to 200 of SEQ ID No 5
- cesA-1a (*Nicotiana tabacum* cellulose synthase cDNA) nucleotides 1 to 195 of SEQ ID No 13
- cesA-2 (*Nicotiana tabacum* cellulose synthase cDNA), AF233893 nucleotides 181 to 385
- als (*Nicotiana* acetolactate synthase cDNA) nucleotides 1 to 207 of SEQ ID No 11

Although the silencing phenotype was predominantly observed in leaf tissue, for some genes silencing was also occasionally observed in other tissues, such as in stems (for pds and gln 1-5), in carpels and sepals of flowers (for pds), in petals and anthers of flowers (for chsA).

It has also been observed that, in plants displaying a gene-silencing phenotype, high levels of chimeric STMV vector and TMV helper RNA accumulated in the roots. For plants displaying a transketolase silencing phenotype in leaves, a significant reduction of transketolase mRNA was observed in roots. These results indicate that tissue- or organ-specific genes, such as flower or root specific genes, can be silenced using the vectors described herein.

Example 6

Vectors With Gene Silencing Inserts of Less Than 100 Nucleotides

In order to test whether target sequences of less than 100 nucleotides would be sufficient to cause gene silencing, the following vectors were constructed:

A 46 bp cDNA fragment of cesA-1a from tobacco (nucleotides 150 to 195 of SEQ ID No 13) was inserted in sense orientation into the polylinker sequence of pVE349, thereby generating pVE439$^{bv349}$.

A 30 bp cDNA fragment of pds from tomato was inserted (in sense orientation) 3' of the 27 bp pds sequence, so that the total size of the pds-insert was 57 bp (nucleotides 1365 to 1421 of SEQ ID No 3), thereby generating vector pVE440.

A 71 bp cDNA fragment of rbcS from tobacco (nucleotides 1 to 71 of SEQ ID No 4) was inserted in sense orientation into the polylinker sequence of pVE349, thereby generating pVE442$^{bv349}$.

Co-inoculation experiments were carried out as described herein above. All three vectors caused the expected gene silencing phenotype, as described previously. These results indicate that the insertion of short target gene fragments, of less than 100 bp, and even of less than 50 bp, is sufficient to cause pronounced gene silencing phenotypes.

Example 7

Modification of the Basic Vectors

When using the two basic vectors pVE349 and pVE350 [described in Example 1(d)] for silencing of endogenous genes, very few, occasional spots of photobleaching were seen, most likely due to a silencing effect caused by the short stretch of 27 nucleotides of the tomato phytoene desaturase sequence, which precedes the polylinker sequence, into which the gene-silencing sequence is inserted.

Although these spots did not interfere with scoring of the gene silencing phenotype, it was tested, whether the occasional spots of photobleaching could be eliminated by shortening the stretch of 27 pds nucleotides preceding the polylinker.

Basic vector pVE349 was, therefore, modified by deleting 5 pds nucleotides of the 27 pds nucleotides, so that only 22 pds nucleotides remained preceding the polylinker sequence, yielding the basic vector pVE359, which comprises the following operationally linked elements:

a nucleotide sequence comprising SEQ ID No 8 (T7 RNA polymerase promoter)

a nucleotide sequence comprising nucleotides 1 to 328 of SEQ ID No 1 a 22 bp fragment of the tomato phytoene desaturase (pds) cDNA comprising nucleotides 1365 to 1386 of SEQ ID No 3 a 25 bp polylinker sequence comprising nucleotides 1 to 25 of SEQ ID No 10 a 22 bp fragment of the tomato phytoene desaturase (pds) cDNA comprising nucleotides 1538 to 1559 of SEQ ID No 3 a nucleotide sequence comprising nucleotides 328 to 1059 of SEQ ID No 1 a nucleotide sequence comprising the reverse compliment of nucleotides 1 to 22 of SEQ ID No 9 (SP6 RNA polymerase promoter)

Basic vector pVE350 was equally modified so that only 22 pds nucleotides remained at the 5'end (rather than 27 nucleotides), yielding the basic vector pVE360, which comprises the following operationally linked elements:

a nucleotide sequence comprising SEQ ID No 8 (T7 RNA polymerase promoter)

a nucleotide sequence comprising nucleotides 1 to 328 of SEQ ID No 1 a 22 bp of the tomato phytoene desaturase (pds) cDNA comprising nucleotides 1365 to 1386 of SEQ ID No 3 a 25 bp polylinker sequence comprising nucleotides 1 to 25 of SEQ ID No 10 a nucleotide sequence comprising nucleotides 603 to 1059 of SEQ ID No 1 a nucleotide sequence comprising the reverse compliment of nucleotides 1 to 22 of SEQ ID No 9 (SP6 RNA polymerase promoter)

After inserting 200 bp antisense fragments of tobacco transketolase cDNA (reverse compliment of nucleotides 1 to 200 of SEQ ID No 5) or a 195 bp sense fragment of tobacco cesA1-a cDNA (nucleotides 1 to 195 of SEQ ID No 13) into the polylinker region of both pVE359 and pVE360 and carrying out tobacco co-infection experiments as described above, it was found that both pVE359 and pVE360 were as efficient in silencing target genes in tobacco as the basic vectors pVE349 and pVE350 were. The only difference was that the occasional spots of photobleaching, seen with pVE349 and pVE350 based vectors, were not seen anymore with pVE359 and pVE360 based vectors.

These results indicated that the pds sequence preceding the gene-silencing construct may vary in length, and may in particular be shorter than 27 nucleotides.

Example 8

Silencing of Two Endogenous Target Genes Using a Single Vector

In order to test whether two endogenous tobacco target genes/gene families could be silenced using a single vector, the following constructs were made:

Vector pVE435$^{bv349}$ was constructed by inserting a 145 bp cDNA fragment of cesA-1a and a 76 bp cDNA fragment of rbcS into the polylinker region of pVE349.

Vector pVE436$^{bv349}$ was constructed by inserting a 58 bp cDNA fragment of pds and a 46 bp fragment of cesA-1a into the polylinker region of pVE349.

Six week old tobacco plants were co-inoculated with the in-vitro transcripts of pVE435$^{bv349}$ or pVE436$^{bv349}$ and TMV helper virus particles. About ten days post inoculation the plants were assessed for the two expected gene silencing phenotypes. Plants showed a double knockout phenotype for each of the vectors. In case of combinatorial rbcS/cesA-1a silencing, leaf sectors showed the chlorotic phenotype typical for rbcS knockouts but also developed lumps, which are specific for cesA-1a knockouts. In plants, which had been silenced for pds and cesA-1a, these lumps also occurred in combination with the bleaching phenotype typical for pds knockouts. These results indicate that at least two endogenous target genes can be silenced using a single vector.

REFERENCES

Amaya et al. (1999) The Plant Cell Vol 11: 1405-1417

An et al. (1996) Plant Journal 10:107-121

Aoyama and Chua (1997) Plant Journal 11:605-612

Ausubel et al. (1994) *Current Protocols in Molecular Biology, Current Protocols*, Vol. 1 and 2, USA.

Baulcombe (1996) Plant Cell 8: 1833-1844

Baulcombe et al. (1998) JIC & SL Annual Report 1996/1997

Baulcombe (1999) Current Opinion in Plant Biology, 2: 109-113

Bouchez and Höfte (1998) Plant Physiol Vol 0.118: 725-732

Brown (1998) *Molecular Biology LabFax*, Volumes I and II, Second Edition, Academic Press (UK)

Burton et al. (2000) The Plant Cell Vol. 12: 691-705

Chapman (1991) PhD dissertation, University of Cambridge, UK

Depicker and Van Montagu (1997) Curr. Opin. Cell. Biol. 9: 373-382

Dhaese et al. 1983; The EMBO Journal 2: 419-426

Dieffenbach and Dveksler (1995) *PCR Primer: A Laboratory Manual*, Cold Spring Harbor Laboratory Press English et al. (1996) Plant Cell 8, 179-188

English et al. (1997) The Plant Journal 12(3): 597-603

Gielen et al. (1984) The EMBO Journal 3: 835-846

Hamilton et al. (1998) The Plant Journal 15(6): 737-746

Henikoff and Henikoff (1992) Proc. Natl. Academy Science 89 (10):915-919

Henkes et al. (2001) The Plant Cell 13: 535-551

Kempin et al. (1997) Nature 389: 802-803

Kumagai et al. (1995) Proc. Natl. Acad. Sci USA 92: 1679-1683

Lu et al. (2000) Poster S22-65, 6th International Congress of Plant Molecular Biology, Quebec June 18-24

Malcuit et al (2000) Poster S22-67, 6th International Congress of Plant Molecular Biology, Quebec June 18-24

Marshall and Hodges (1998) Nature Biotechnology Vol. 16: 27-31

McPherson et al. (2000) *PCR—Basics: From Background to Bench*, First Edition, Springer Verlag, Germany Needleman and Wunsch algorithm (1970) J. Mol. Biol. 48: 443-453

Pereira and Aerts (1998) Methods in Molecular Biology 82 Eds. Martinez-Zapatar and Salinas, Humana Press, NJ R. D. D. Croy (1993) Plant Molecular Biology Labfax jointly published by BIOS Scientific Publications Ltd (UK) and Blackwell Scientific Publications, UK.

Ramsay (1998) Nature Biotechnology Vol.16: 40-44

Ruiz et al. (1998) The Plant Cell 10: 937-946

Sambrook et al. (1989) Molecular Cloning: A Laboratory Manual, Second Edition, Cold Spring Harbor Laboratory Press, NY Sambrook and Russell (2001) *Molecular Cloning: A Laboratory Manual*, Third Edition, Cold Spring Harbor Laboratory Press, NY Stam et al. (1997) Ann. Botan. 79:3-12

Severin and Schoeffl (1990) PMB 15: 825-833

Smith and Waterman (1981) Advances in Applied Mathematics 2: 482-489

Velten et al. 1985 Nucleic Acids Research 13: 6981-6998

Walkey (1985) Applied Virology, William Heinemann Ltd, London

Waterhouse et al. (1998) Proc. Natl. Acad. Sci USA 95: 13959-13964

Wilbur and Lipmann (1983) Proc. Nat. Acad. Sci. USA 80: 726

What is claimed is:

1. A method for introducing inhibitory RNA into a plant cell, plant tissue, or plant, said method comprising (a) providing a viral RNA vector derived from satellite tobacco mosaic virus (STMV), and (b) infecting the plant cell, plant tissue, or plant with said viral RNA vector and a corresponding helper virus, wherein said viral RNA vector comprises in sequence (1) the nucleotide sequence encoding the polypeptide consisting of the N-terminal third of the amino acids of the STMV coat protein, (2) a nucleotide sequence comprising at least 27 contiguous nucleotides of nucleotides 1365 to 1394 of SEQ ID NO: 3, (3) a gene-silencing construct comprising a nucleotide sequence of at least 27 contiguous nucleotides of a target gene within the plant cell, plant tissue, or plant, which when transcribed yields said inhibitory RNA, and (4) a nucleotide sequence comprising nucleotides 603 to 1059 of SEQ ID NO: 1.

2. The method according to claim 1, wherein the target gene is an endogenous gene or a transgene.

3. A method according to claim 1, wherein the nucleotide sequence encoding the polypeptide consisting of the N-terminal third of the amino acids of the STMV coat protein includes at least the sequence of nucleotides 162 to 328 of SEQ ID NO: 1.

4. A method according to claim 1, wherein the viral RNA vector comprises nucleotides 1365 to 1391 of SEQ ID NO: 3.

5. A method according to claim 1, wherein the viral RNA vector comprises nucleotides 1365 to 1394 of SEQ ID NO: 3.

6. A method according to claim 1, wherein said gene-silencing construct comprises antisense RNA.

7. A method according to claim 1, wherein said gene-silencing construct comprises sense RNA.

8. A method according to claim 1, wherein said gene-silencing construct comprises an inverted repeat.

9. The method according to claim 1, wherein said plant cell, plant tissue, or plant is *Nicotiana* spp, *Solanacea, Oryza sativa, Zea mays, Brassica* spp., *Gossypum* spp., *Triticum* spp., *Arabidopsis* spp., or *Petunia* spp.

10. A viral RNA vector derived from satellite tobacco mosaic virus (STMV), said viral RNA vector comprising in sequence:

(1) the nucleotide sequence encoding the polypeptide consisting of the N-terminal third of the amino acids of the STMV coat protein; and (2) a nucleotide sequence comprising at least 27 contiguous nucleotides of nucleotides 1365 to 1394 of SEQ ID NO: 3, (3) a polylinker sequence, and (4) a nucleotide sequence comprising nucleotides 603 to 1059 of SEQ ID NO: 1.

11. A viral RNA vector according to claim 10, further comprising a gene-silencing construct.

12. A viral RNA vector according to claim 11, wherein said gene-silencing construct comprises at least about 50 nucleotides.

13. A cDNA copy of a viral RNA vector according to claim 10.

14. A kit for introducing inhibitory RNA into a plant cell, plant tissue, or plant, said kit comprising:

a) a viral RNA vector according to claim 10; and b) a corresponding helper virus.

15. A kit for introducing inhibitory RNA into a plant cell, plant tissue, or plant, said kit comprising:

a) a cDNA copy of an RNA vector according to claim 13; and b) a corresponding helper virus.

16. A kit according to claim 14, wherein said corresponding helper virus is tobacco mild green mosaic virus.

17. A kit according to claim 15, wherein said corresponding helper virus is tobacco mild green mosaic virus.

18. A method for introducing inhibitory RNA into a plant cell, plant tissue, or plant, said method comprising:

a) providing a T-DNA vector comprising between right- and left-border sequences the following operationally linked elements:

a promoter, a DNA sequence which, when transcribed, yields a viral RNA vector and a 3' non-translated sequence, wherein said viral RNA vector is derived from satellite tobacco mosaic virus (STMV) and comprises in sequence (1) the nucleotide sequence encoding the polypeptide consisting of the N-terminal third of the amino acids of the STMV coat protein, (2) a nucleotide sequence comprising at least 27 contiguous nucleotides of nucleotides 1365 to 1394 of SEQ ID NO: 3, (3) a gene-silencing construct comprising a nucleotide sequence of at least 27 contiguous nucleotides of a target gene within the plant cell, plant tissue, or plant, which when transcribed yields said inhibitory RNA, and (4) a nucleotide sequence comprising nucleotides 603 to 1059 of SEQ ID NO: 1;

b) introducing said T-DNA vector into an Agrobacterium strain; and c) infecting the plant cell, plant tissue, or plant with a corresponding helper virus or helper virus RNA and infiltrating said plant cell, plant tissue, or plant with said Agrobacterium strain.

19. A method for introducing inhibitory RNA into a plant cell comprising:

(a) introducing a gene silencing construct in the viral RNA vector of the kit of claim 14, and (b) using said kit to introduce inhibitory RNA into a plant cell.

20. A method for introducing inhibitory RNA into a plant cell comprising (a) introducing a gene silencing construct in the cDNA copy of a viral RNA vector of the kit of claim 15, and (b) using said kit to introduce inhibitory RNA into a plant cell.

21. The method according to claim 1, wherein said at least 27 contiguous nucleotides are different from at least 27 contiguous nucleotides of SEQ ID No. 3.

22. A viral RNA vector according to claim 11, wherein said gene-silencing construct comprises 50 to 250 nucleotides.

23. The method according to claim 18, wherein said plant cell, plant tissue, or plant is from a *Nicotiana* spp., *Solanacea, Oryza sativa, Zea mays, Brassica* spp., *Gossypum* spp., *Triticum* spp., *Arabidopsis* spp., or *Petunia spp.*

24. The method of claim 1, further comprising the following steps:

(a) waiting until said introduction of said inhibitory RNA yields initial gene-silencing symptoms in the tissue of said plant;

(b) removing the apical meristem of the main stem of said plant; and (c) identifying amongst newly developing plant tissue of said plant, tissue with an altered phenotype.

* * * * *